US012623092B2

(12) United States Patent
Lachaine et al.

(10) Patent No.: US 12,623,092 B2
(45) Date of Patent: May 12, 2026

(54) DYNAMIC ADAPTATION OF RADIOTHERAPY TREATMENT PLANS

(71) Applicant: Elekta LTD., Montreal (CA)

(72) Inventors: Martin Emile Lachaine, Montreal (CA); Tony Falco, La Prairie (CA)

(73) Assignee: Elekta LTD., Montreal (CA)

( * ) Notice: Subject to any disclaimer, the term of this patent is extended or adjusted under 35 U.S.C. 154(b) by 493 days.

(21) Appl. No.: 18/180,491

(22) Filed: Mar. 8, 2023

(65) Prior Publication Data

US 2023/0285776 A1 Sep. 14, 2023

(30) Foreign Application Priority Data

Mar. 9, 2022 (GB) ..................................... 2203310

(51) Int. Cl.
*A61N 5/10* (2006.01)

(52) U.S. Cl.
CPC ......... *A61N 5/1038* (2013.01); *A61N 5/1049* (2013.01); *A61N 5/1067* (2013.01)

(58) Field of Classification Search
None
See application file for complete search history.

(56) References Cited

U.S. PATENT DOCUMENTS

2016/0310761 A1* 10/2016 Li ......................... A61N 5/1039

FOREIGN PATENT DOCUMENTS

| EP | 3628372 | 4/2020 |
| GB | 2616458 | 12/2024 |
| WO | WO-2017167794 A1 | 10/2017 |
| WO | 2021001052 | 1/2021 |

OTHER PUBLICATIONS

"United Kingdom Application Serial No. 2203310.4, First Examination Report Under Section 18(3) mailed Mar. 4, 2024", 2 pgs.
"United Kingdom Application Serial No. 2203310.4, Search Report mailed Aug. 26, 2022", 3 pgs.
"United Kingdom Application Serial No. 2203310.4, Response filed Sep. 4, 2024 to First Examination Report Under Section 183 mailed Mar. 4, 2024", 16 pgs.

* cited by examiner

*Primary Examiner* — Hoon K Song
(74) *Attorney, Agent, or Firm* — Schwegman Lundberg & Woessner, P.A.

(57) ABSTRACT

A reference radiotherapy treatment plan having a plurality of control points, such as a sequence of gantry angles, aperture leaf positions, and intensity weights, can be adapted during the radiotherapy treatment session. Treatment imaging data of a patient may be obtained during the radiotherapy treatment session and one or more parameters may be determined using the treatment imaging data. Then, a current radiotherapy treatment plan may be generated based on the parameter(s). The reference radiotherapy treatment plan for the radiotherapy treatment session may be modified during the radiotherapy treatment session by updating one of the plurality of control points of the reference radiotherapy treatment plan with a control point of a current radiotherapy treatment plan, which may compensate for patient deformations during the delivery of radiotherapy treatment, or intrafraction patient deformations and thereby improve the delivery accuracy and efficacy of radiation doses to a patient undergoing radiotherapy treatment.

27 Claims, 10 Drawing Sheets

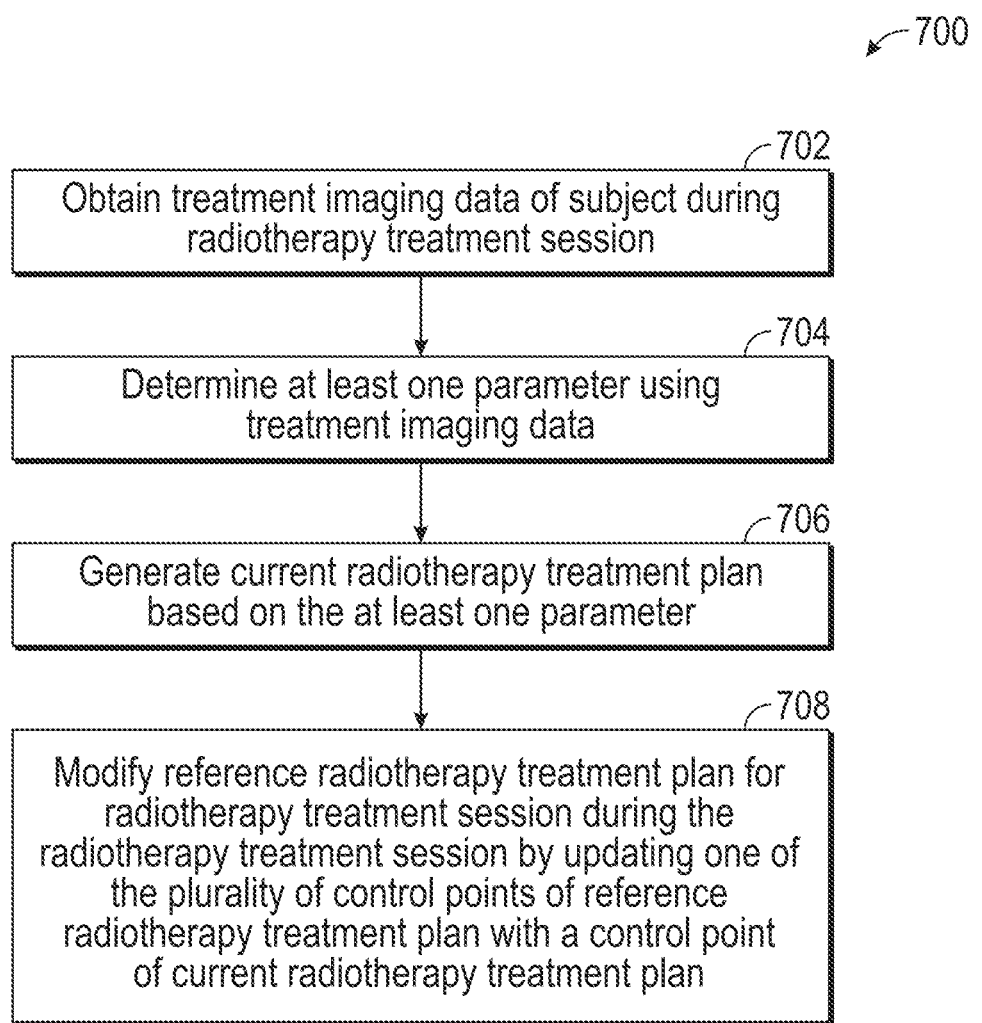

700

702
Obtain treatment imaging data of subject during radiotherapy treatment session 704
Determine at least one parameter using treatment imaging data 706
Generate current radiotherapy treatment plan based on the at least one parameter 708
Modify reference radiotherapy treatment plan for radiotherapy treatment session during the radiotherapy treatment session by updating one of the plurality of control points of reference radiotherapy treatment plan with a control point of current radiotherapy treatment plan

FIG. 7

DYNAMIC ADAPTATION OF RADIOTHERAPY TREATMENT PLANS

CLAIM FOR PRIORITY

This application claims the benefit of priority of British Application No. 2203310.4, filed Mar. 9, 2022, which is hereby incorporated by reference in its entirety.

TECHNICAL FIELD

Embodiments of the present disclosure pertain generally to radiotherapy treatment sessions and specifically to imaging techniques.

BACKGROUND

Radiation therapy (or "radiotherapy") may be used to treat cancers or other ailments in mammalian (e.g., human and animal) tissue. One such radiotherapy technique involves irradiation with a Gamma Knife, whereby a patient is irradiated by a large number of low-intensity gamma ray beams that converge with high intensity and high precision at a target (e.g., a tumor). In another embodiment, radiotherapy is provided using a linear accelerator, whereby a tumor is irradiated by high-energy particles (e.g., electrons, protons, ions, high-energy photons, and the like). The placement and dose of the radiation beam must be accurately controlled to ensure the tumor receives the prescribed radiation, and the placement of the beam should be such as to minimize damage to the surrounding healthy tissue, often called the organ(s) at risk (OARs). Radiation is termed "prescribed" because a physician orders a predefined amount of radiation to the tumor and surrounding organs similar to a prescription for medicine. Generally, ionizing radiation in the form of a collimated beam is directed from an external radiation source toward a patient.

A specified or selectable beam energy may be used, such as for delivering a diagnostic energy level range or a therapeutic energy level range. Modulation of a radiation beam may be provided by one or more attenuators or collimators (e.g., a multi-leaf collimator (MLC)). The intensity and shape of the radiation beam may be adjusted by collimation to avoid damaging healthy tissue (e.g., OARs) adjacent to the targeted tissue by conforming the projected beam to a profile of the targeted tissue.

The treatment planning procedure may include using a three-dimensional (3D) image of the patient to identify a target region (e.g., the tumor) and to identify critical organs near the tumor. Creation of a treatment plan may be a time-consuming process where a planner tries to comply with various treatment objectives or constraints (e.g., dose volume histogram (DVH), overlap volume histogram (OVH)), taking into account their individual importance (e.g., weighting) in order to produce a treatment plan that is clinically acceptable. This task may be a time-consuming trial-and-error process that is complicated by the various OARs because as the number of OARs increases (e.g., up to thirteen for a head-and-neck treatment), so does the complexity of the process. OARs distant from a tumor may be easily spared from radiation, while OARs close to or overlapping a target tumor may be difficult to spare.

Traditionally, for each patient, the initial treatment plan may be generated in an "offline" manner. The treatment plan may be developed well before radiation therapy is delivered, such as using one or more medical imaging techniques. Imaging information may include, for example, images from X-rays, computed tomography (CT), nuclear magnetic resonance (MR), positron emission tomography (PET), single-photon emission computed tomography (SPECT), or ultrasound. A health care provider, such as a physician, may use 3D imaging information indicative of the patient anatomy to identify one or more target tumors along with the OARs near the tumor(s). The health care provider may delineate the target tumor that is to receive a prescribed radiation dose using a manual technique, and the health care provider may similarly delineate nearby tissue, such as organs, at risk of damage from the radiation treatment. Alternatively, or additionally, an automated tool (e.g., ABAS provided by Elekta AB, Sweden) may be used to assist in identifying or delineating the target tumor and organs at risk. A radiation therapy treatment plan ("treatment plan") may then be created using an optimization technique based on clinical and dosimetric objectives and constraints (e.g., the maximum, minimum, and fraction of dose of radiation to a fraction of the tumor volume ("95% of target shall receive no less than 100% of prescribed dose"), and like measures for the critical organs). The optimized plan is comprised of numerical parameters that specify the direction, cross-sectional shape, and intensity of each radiation beam.

The treatment plan may then be later executed by positioning the patient in the treatment machine and delivering the prescribed radiation therapy directed by the optimized plan parameters. The radiation therapy treatment plan may include dose "fractioning," whereby a sequence of radiation treatments is provided over a predetermined period of time (e.g., 30-45 daily fractions), with each treatment including a specified fraction of a total prescribed dose. However, during treatment, the position of the patient and the position of the target tumor in relation to the treatment machine (e.g., linear accelerator—"linac") is very important in order to ensure the target tumor and not healthy tissue is irradiated.

Since most patients receive more than one fraction of radiation as part of a course of therapy, and because the anatomy may change (deform) between these fractions, it is not straightforward to sum the doses delivered during the individual fractions so the physician may accurately gauge how the treatment is proceeding relative to the original intent as defined by the prescription.

OVERVIEW

This disclosure describes techniques for adaptation of a reference radiotherapy treatment plan having a plurality of control points during the radiotherapy treatment session. Treatment imaging data of the subject, e.g., patient, may be obtained during the radiotherapy treatment session and one or more parameters may be determined using the treatment imaging data. Then, a current radiotherapy treatment plan may be generated based on the parameter(s). The reference radiotherapy treatment plan for the radiotherapy treatment session may be modified during the radiotherapy treatment session by updating one of the plurality of control points of the reference radiotherapy treatment plan with a control point of a current radiotherapy treatment plan, which may compensate for patient deformations during the delivery of radiotherapy treatment, or intrafraction patient deformations and thereby improve the delivery accuracy and efficacy of radiation doses to a patient undergoing radiotherapy treatment.

In some aspects, this disclosure is directed to a computer-implemented method for adaptation of a reference radiotherapy treatment plan having a plurality of control points, performed on a subject in a radiotherapy treatment session, the computer-implemented method comprising: obtaining treatment imaging data of the subject during the radiotherapy treatment session; determining at least one parameter using the treatment imaging data; generating a current radiotherapy treatment plan based on the at least one parameter; and modifying the reference radiotherapy treatment plan for the radiotherapy treatment session during the radiotherapy treatment session by updating one of the plurality of control points of the reference radiotherapy treatment plan with a control point of the current radiotherapy treatment plan.

In some aspects, this disclosure is directed to a radiotherapy system for adaptation of a reference radiotherapy treatment plan having a plurality of control points, performed on a subject in a radiotherapy treatment session, the radiotherapy system comprising: an image acquisition device configured to acquire measurements of the subject during the radiotherapy treatment session; a processor configured to: perform, at a first rate, a first computational loop to generate at least one parameter using the acquired measurements, wherein the at least one parameter represents an anatomical state of the subject; perform, at a second rate that is independent of the first rate, a second computational loop to generate a current radiotherapy treatment plan based on the at least one parameter, wherein the current radiotherapy treatment plan includes a plurality of control points; and modify a reference radiotherapy treatment plan for the radiotherapy treatment session during the radiotherapy treatment session by updating a control point of the reference radiotherapy treatment plan with the control point of the current radiotherapy treatment plan; and a radiotherapy device configured to deliver a dose of radiation to an anatomical region of interest using the current radiotherapy treatment plan.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example but not by way of limitation, various embodiments discussed in the present document.

FIG. 7 illustrates a flow diagram of an example of a computer-implemented method for adaptation of a reference radiotherapy treatment plan having a plurality of control points, performed on a subject in a radiotherapy treatment session, according to some embodiments of the present disclosure.

DETAILED DESCRIPTION

Figure 1:
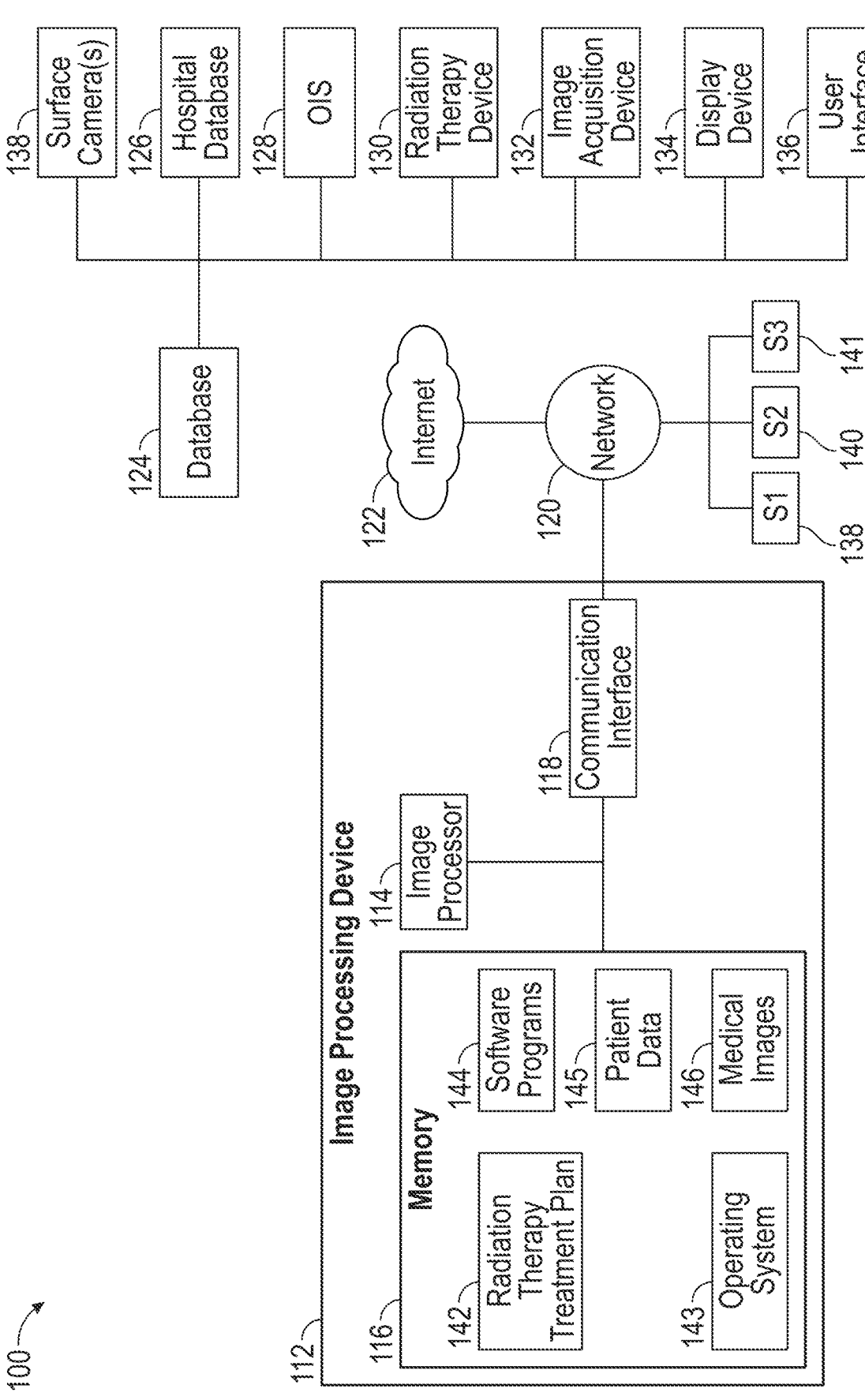
FIG. 1 illustrates an example of a radiotherapy system, according to some embodiments of the present disclosure.

In the following detailed description, reference is made to the accompanying drawings which form a part hereof, and which is shown by way of illustration-specific embodiments in which the present disclosure may be practiced. These embodiments, which are also referred to herein as "examples," are described in sufficient detail to enable those skilled in the art to practice the disclosure, and it is to be understood that the embodiments may be combined, or that other embodiments may be utilized, and that structural, logical and electrical changes may be made without departing from the scope of the present disclosure. The following detailed description is, therefore, not be taken in a limiting sense, and the scope of the present disclosure is defined by the appended claims and their equivalents.

In an approach to non-adaptive radiotherapy, a diagnostic quality simulation computed tomography (CT) dataset may be acquired as a primary imaging dataset for radiation treatment planning. A simulation CT may provide two key inputs for generating a radiation treatment plan: a structure set and an Electron Density (ED) map. The structure set may include the target, organs-at-risk, and external contour, as well as certain other structures of interest. In some cases, complementary secondary datasets such as MM or PET may be used, such as to assist with structure definition. The ED map may be assigned on a voxel-by-voxel basis by a calibration curve that relates CT numbers to ED values, or average ED values may be assigned to corresponding individual structures.

The radiation treatment planning may generate a patient prescription. The patient prescription may include specification of a number of individual treatment "fractions" in which the course of radiation treatment is to be delivered over a course of time that may include inpatient or outpatient treatment sessions. In one approach to non-adaptive radiotherapy, it is assumed that the patient anatomy does not deform significantly from fraction-to-fraction, and so the same treatment plan is delivered at each fraction. Images such as cone-beam CT (CBCT) may be acquired during such fraction treatment sessions, but they are only used to improve patient alignment for a radiation treatment session, not to modify the treatment plan, such as in view of a change in patient anatomy.

Patient anatomy is known to deform from one treatment session to the next, which may significantly compromise the dose distribution as intended by the initial treatment plan. Online adaptive radiotherapy may adapt the treatment plan, such as to better conform to the deformable patient anatomy for each fraction.

Online adaptive radiotherapy may involve a) acquiring a new 3D session image, such as a cone-beam CT (CBCT) or magnetic resonance (MR) image during each treatment session; b) determining anatomic deformations between the planning and the treatment session; and c) modifying the radiotherapy treatment plan to compensate for any degradations in the dose distributions caused by the anatomic deformations.

The current state of the art of online adaptive radiotherapy may be considered 'static' in the sense that it only corrects for anatomic deformations that occur from session to session (interfraction motion). Online adaptive radiotherapy does not correct for intrafraction motion, i.e., anatomic deformations that occur during the actual treatment delivery itself. The latter could be considered 'dynamic' online adaptive radiotherapy because it would dynamically modify the treatment plan, ensuring that degradations caused by anatomic deformations are compensated continuously at every moment.

In static online adaptive radiotherapy, a 3D session image (or 3D reference image) is generally first acquired in the treatment room, and the initial (or reference) radiotherapy treatment plan is adapted to better conform to this 3D reference image. The 3D reference image may be referred to as $I_{ref}$ and the associated reference radiotherapy treatment plan as $P_{ref}$. The reference radiotherapy treatment plan $P_{ref}$ includes, for example, a sequence of gantry angles, aperture leaf positions, and intensity weights that are collectively referred to as the control points $$A_m^{ref}$$

for m=1 . . . M. The reference radiotherapy treatment plan may be considered as the set of all control points, $$P_{ref} = \{A_1^{ref}, A_2^{ref}, \dots, A_M^{ref}\}.$$

In a static online adaptive radiotherapy treatment session, the control points $$A_m^{ref}$$

are delivered in sequence of increasing m until they have all been delivered. For a dynamic online adaptive radiotherapy session, at each new time point $t_i$, each control point $$A_m^{ref}$$

may be dynamically modified to a new control point $$A_m^i$$

on-the-fly' to account for patient motion.

If the radiotherapy system could determine the updated patient image at each time point, $I_i$, then the radiotherapy system could adapt the original (reference) radiotherapy treatment plan $P_{ref}$ to a new, adapted (current) radiotherapy treatment plan $P_i$. So, in a simple example, at time $t_1$, such a radiotherapy system would generate an updated patient image $I_1$, use this image to generate an adapted radiotherapy treatment plan $P_1$, and treat a subject with its updated first control point $$A_1^1$$

instead of the originally scheduled reference control point $$A_1^{ref}.$$

At the next time point $t_2$, such a radiotherapy system would generate an updated patient image $I_2$, use this image to generate an adapted treatment plan $P_2$, and treat the subject with its updated second control point $$A_2^2$$

instead of the originally scheduled reference control point $$A_2^{ref}.$$

The radiotherapy system would continue with this process until all of the modified control points had been delivered.

Some issues with this method include the following. First, the radiotherapy system may not be able to obtain a full 3D image $I_i$ with sufficient speed. For example, it may take a CBCT or 3D MRI on the order of minutes to acquire such an image. Second, once the radiotherapy system acquired the full 3D image $I_i$, it may take the radiotherapy system minutes to find an adapted radiotherapy treatment plan $P_i$. Third, the adapted radiotherapy treatment plan $P_i$ may be significantly different than the reference radiotherapy treatment plan $P_{ref}$, with no correspondence between the control points of both plans and thus no clear way to replace the originally scheduled control point with a control point from the newly adapted radiotherapy treatment plan. Fourth, even if the radiotherapy system was able to generate images $I_i$ and adapted radiotherapy treatment plans $P_i$ with sufficient speed, they would likely be generated at different rates and lags, so it would be difficult to synchronize image acquisition, plan adaptation, and update the control points for treatment.

Unfortunately, dynamic online adaptive radiotherapy, which dynamically modifies the treatment plan and ensures that degradations caused by anatomic deformations are compensated continuously at every moment, is not practiced today. Some techniques utilize 'MLC tracking' as a potential achievable implementation of dynamic online adaptive radiotherapy. With MLC tracking, the MLC apertures are continuously shifted (geometrically) to follow the target centroid. MLC tracking may be a useful tool for some clinical cases, but some limitations include the following: a) it is very difficult to verify the actual dose distribution delivered to the patient, and b) it does not take into account intrafraction patient deformations, and thus may compromise the dose distribution to the patient.

In theory, if real-time anatomical deformations are known, it should be possible to re-optimize the MLC positions continuously as the patient anatomy is updated. For respiratory motion, the plan would need to be re-optimized at least every 500 ms, preferably <100 ms. This is not currently achievable in practice because it may take 1-10 minutes to re-optimize a treatment plan. The present inventors have recognized a need for a method for dynamic online adaptive radiotherapy that compensates for patient deformations during the delivery of radiotherapy treatment, or intrafraction patient deformations.

This disclosure describes techniques for adaptation of a reference radiotherapy treatment plan having a plurality of control points during the radiotherapy treatment session. Treatment imaging data of the subject, e.g., patient, may be obtained during the radiotherapy treatment session and one or more parameters may be determined using the treatment imaging data. Then, a current radiotherapy treatment plan may be generated based on the parameter(s). The reference radiotherapy treatment plan for the radiotherapy treatment session may be modified during the radiotherapy treatment session by updating one of the plurality of control points of the reference radiotherapy treatment plan with a control point of a current radiotherapy treatment plan, which may compensate for patient deformations during the delivery of radiotherapy treatment, or intrafraction patient deformations and thereby improve the delivery accuracy and efficacy of radiation doses to a patient undergoing radiotherapy treatment. In some examples, the techniques of this disclosure may determine a relationship between the reference radiotherapy treatment plan and the degrees of freedom in a patient's respiratory motion, and update the reference radiotherapy treatment plan using that relationship.

FIG. 1 illustrates an example of a radiotherapy system 100 for providing radiation therapy to a patient. The radiotherapy system 100 includes an image processing device 112. The image processing device 112 may be connected to a network 120. The network 120 may be connected to the Internet 122. The network 120 may connect the image processing device 112 with one or more of a database 124, a hospital database 126, an oncology information system (OIS) 128, a radiation therapy device 130, an image acquisition device 132, a display device 134, a user interface 136, and one or more surface cameras 138, such as surface cameras 138A-138C in FIG. 2A and/or surface camera 138D in FIG. 2B. Examples of surface cameras 138 may include those manufactured by C-Rad, VisionRT, and Varian HumediQ. The surface camera(s) 138 (e.g., one or more 2D or 3D cameras) may be used to acquire real-time images of the surface of a patient's body (e.g., the patient's skin) while medical images are being acquired. Because the surface imaging is taken at the same time as the medical imaging, the surface imaging may provide a more accurate definition of the location of the boundaries of the patient's body while the medical imaging was taken. The image processing device 112 may be configured to generate radiation therapy treatment plans 142 to be used by the radiation therapy device 130.

The image processing device 112 may include a memory device 116, an image processor 114, and a communication interface 118. The memory device 116 may store computer-executable instructions, such as an operating system 143, radiation therapy treatment plans 142 (e.g., original treatment plans, adapted treatment plans and the like), software programs 144 (e.g., artificial intelligence, deep learning, neural networks, radiotherapy treatment plan software), and any other computer-executable instructions to be executed by the image processor 114.

In one embodiment, the software programs 144 may convert medical images of one format (e.g., MRI) to another format (e.g., CT) by producing synthetic images, such as pseudo-CT images. For instance, the software programs 144 may include image processing programs to train a predictive model for converting a medical image 146 in one modality (e.g., an MRI image) into a synthetic image of a different modality (e.g., a pseudo CT image); alternatively, the trained predictive model may convert a CT image into an MM image.

In another embodiment, the software programs 144 may register the patient image (e.g., a CT image or an MR image) with that patient's dose distribution (also represented as an image) so that corresponding image voxels and dose voxels are associated appropriately by the network.

In yet another embodiment, the software programs 144 may substitute functions of the patient images or processed versions of the images that emphasize some aspect of the image information. Such functions might emphasize edges or differences in voxel textures, or any other structural aspect useful to neural network learning.

In another embodiment, the software programs 144 may substitute functions of the dose distribution that emphasize some aspect of the dose information. Such functions might emphasize steep gradients around the target or any other structural aspect useful to neural network learning. The memory device 116 may store data, including medical images 146, patient data 145, and other data required to create and implement a radiation therapy treatment plan 142.

In yet another embodiment, the software programs 144 may generate a structural estimate (e.g., a 3D model of the region of interest) using an iterative image reconstruction process. The structural estimate may be or include an X-ray attenuation map that represents a 3D model of a region of interest. The structural estimate may be used to estimate or simulate X-ray measurements to be compared with real X-ray measurements for updating the structural estimate. Specifically, the software programs 144 may access a current structural estimate of the region of interest and generate a first simulated X-ray measurement based on the current structural estimate of the region of interest.

A simulated X-ray measurement, as referred to herein, represents the expected output of an X-ray detector element when an X-ray source projects one or more X-ray beams through the region of interest towards the X-ray detector element. The simulated X-ray measurement may provide an expected image output that is to be received from the X-ray detector element.

The software programs 144 may receive a first real X-ray measurement from a CBCT system (or other CT imaging system, such as an enclosed gantry helical multi-slice CT with a curved detector or tomotherapy system) and generate an update to the current structural estimate of the region of interest as a function of the first simulated X-ray measurement and the first real X-ray measurement. A real X-ray measurement, as referred to herein, is an actual output that is received from a CBCT system (or other CT imaging system, such as an enclosed gantry helical multi-slice CT with a curved detector or tomotherapy system) that represents the amount of signal generated by X-rays in the detector along different directions, such as in an image form.

The update may be generated invariant on (independent of) the current structural estimate. The structural estimate may be used to control one or more radiotherapy treatment parameters by recalculating dose, adjusting one or more radiotherapy treatment machine parameters, or generating a display of the structural estimate on a graphical user interface.

In addition to the memory device 116 storing the software programs 144, it is contemplated that software programs 144 may be stored on a removable computer medium, such as a hard drive, a computer disk, a CD-ROM, a DVD, a HD, a Blu-Ray DVD, USB flash drive, a SD card, a memory stick, or any other suitable medium; and the software programs 144 when downloaded to image processing device 112 may be executed by image processor 114.

The processor 114 may be communicatively coupled to the memory device 116, and the processor 114 may be configured to execute computer-executable instructions stored thereon. The processor 114 may send or receive medical images 146 to memory device 116. For example, the processor 114 may receive medical images 146 from the image acquisition device 132 via the communication interface 118 and network 120 to be stored in memory device 116. The processor 114 may also send medical images 146 stored in memory device 116 via the communication interface 118 to the network 120 be either stored in database 124 or the hospital database 126.

Further, the processor 114 may utilize software programs 144 (e.g., a treatment planning software) along with the medical images 146 and patient data 145 to create the radiation therapy treatment plan 142. Medical images 146 may include information such as imaging data associated with a patient anatomical region, organ, or volume of interest segmentation data. Patient data 145 may include information such as (1) functional organ modeling data (e.g., serial versus parallel organs, appropriate dose response models, etc.); (2) radiation dosage data (e.g., DVH information); or (3) other clinical information about the patient and course of treatment (e.g., other surgeries, chemotherapy, previous radiotherapy, etc.).

In addition, the processor 114 may utilize software programs to generate intermediate data such as updated parameters to be used, for example, by a machine learning model, such as a neural network model; or generate intermediate 2D or 3D images, which may then subsequently be stored in memory device 116. The processor 114 may subsequently transmit the executable radiation therapy treatment plan 142 via the communication interface 118 to the network 120 to the radiation therapy device 130, where the radiation therapy plan will be used to treat a patient with radiation. In addition, the processor 114 may execute software programs 144 to implement functions such as image conversion, image segmentation, deep learning, neural networks, and artificial intelligence. For instance, the processor 114 may execute software programs 144 that train or contour a medical image; such software programs 144 when executed may train a boundary detector or utilize a shape dictionary.

The processor 114 may be a processing device, including one or more general-purpose processing devices such as a microprocessor, a central processing unit (CPU), a graphics processing unit (GPU), an accelerated processing unit (APU), or the like. More particularly, the processor 114 may be a complex instruction set computing (CISC) microprocessor, a reduced instruction set computing (RISC) microprocessor, a very long instruction Word (VLIW) microprocessor, a processor implementing other instruction sets, or processors implementing a combination of instruction sets. The processor 114 may also be implemented by one or more special-purpose processing devices such as an application-specific integrated circuit (ASIC), a field programmable gate array (FPGA), a digital signal processor (DSP), a System on a Chip (SoC), or the like. As would be appreciated by those skilled in the art, in some embodiments, the processor 114 may be a special-purpose processor rather than a general-purpose processor. The processor 114 may include one or more known processing devices, such as a microprocessor from the Pentium™, Core™, Xeon™, or Itanium® family manufactured by Intel™, the Turion™, Athlon™, Sempron™, Opteron™ FX™ Phenom™ family manufactured by AMD™, or any of various processors manufactured by Sun Microsystems. The processor 114 may also include graphical processing units such as a GPU from the GeForce®, Quadro®, Tesla® family manufactured by Nvidia™, GMA, Iris™ family manufactured by Intel™, or the Radeon™ family manufactured by AMD™. The processor 114 may also include accelerated processing units such as the Xeon Phi™ family manufactured by Intel™. The disclosed embodiments are not limited to any type of processor(s) otherwise configured to meet the computing demands of identifying, analyzing, maintaining, generating, and/or providing large amounts of data or manipulating such data to perform the methods disclosed herein. In addition, the term "processor" may include more than one processor (for example, a multi-core design or a plurality of processors each having a multi-core design). The processor 114 may execute sequences of computer program instructions, stored in memory device 116, to perform various operations, processes, methods that will be explained in greater detail below.

The memory device 116 may store medical images 146. In some embodiments, the medical images 146 may include one or more MRI images (e.g., 2D MM, 3D MRI, 2D streaming MM, four-dimensional (4D) MRI, 4D volumetric MRI, 4D cine MRI, etc.), functional MM images (e.g., fMRI, DCE-MRI, diffusion MRI), CT images (e.g., 2D CT, cone beam CT, 3D CT, 4D CT), ultrasound images (e.g., 2D ultrasound, 3D ultrasound, 4D ultrasound), one or more projection images representing views of an anatomy depicted in the MM, synthetic CT (pseudo-CT), and/or CT images at different angles of a gantry relative to a patient axis, PET images, X-ray images, fluoroscopic images, radiotherapy portal images, SPECT images, computer generated synthetic images (e.g., pseudo-CT images), aperture images, graphical aperture image representations of MLC leaf positions at different gantry angles, and the like. Further, the medical images 146 may also include medical image data, for instance, training images, ground truth images, contoured images, and dose images. In an embodiment, the medical images 146 may be received from the image acquisition device 132. Accordingly, image acquisition device 132 may include an MRI imaging device, a Megavolt (MV) imaging device, a CT imaging device, a CBCT imaging device, a PET imaging device, an ultrasound imaging device, a fluoroscopic device, a SPECT imaging device, an integrated linac and MRI imaging device, an integrated linac and CT imaging device, an integrated linac and CBCT imaging device, or other medical imaging devices for obtaining the medical images of the patient. The medical images 146 may be received and stored in any type of data or any type of format that the image processing device 112 may use to perform operations consistent with the disclosed embodiments.

The memory device 116 may be a non-transitory computer-readable medium, such as a read-only memory (ROM), a phase-change random access memory (PRAM), a static random access memory (SRAM), a flash memory, a random access memory (RAM), a dynamic random access memory (DRAM) such as synchronous DRAM (SDRAM), an electrically erasable programmable read-only memory (EEPROM), a static memory (e.g., flash memory, flash disk, static random access memory) as well as other types of random access memories, a cache, a register, a CD-ROM, a DVD or other optical storage, a cassette tape, other magnetic storage device, or any other non-transitory medium that may be used to store information including image, data, or computer-executable instructions (e.g., stored in any format) capable of being accessed by the processor 114, or any other type of computer device. The computer program instructions may be accessed by the processor 114, read from the ROM, or any other suitable memory location, and loaded into the RAM for execution by the processor 114. For example, the memory device 116 may store one or more software applications. Software applications stored in the memory device 116 may include, for example, an operating system 143 for common computer systems as well as for software-controlled devices. Further, the memory device 116 may store an entire software application, or only a part of a software application, that is executable by the processor 114. For example, the memory device 116 may store one or more radiation therapy treatment plans 142.

The image processing device 112 may communicate with the network 120 via the communication interface 118, which may be communicatively coupled to the processor 114 and the memory device 116. The communication interface 118 may provide communication connections between the image processing device 112 and radiotherapy system 100 components (e.g., permitting the exchange of data with external devices). For instance, the communication interface 118 may, in some embodiments, have appropriate interfacing circuitry to connect to the user interface 136, which may be a hardware keyboard, a keypad, or a touch screen through which a user may input information into radiotherapy system 100.

Communication interface 118 may include, for example, a network adaptor, a cable connector, a serial connector, a USB connector, a parallel connector, a high-speed data transmission adaptor (e.g., such as fiber, USB 3.0, thunderbolt, and the like), a wireless network adaptor (e.g., such as a WiFi adaptor), a telecommunication adaptor (e.g., 3G, 4G/LTE and the like), and the like. Communication interface 118 may include one or more digital and/or analog communication devices that permit image processing device 112 to communicate with other machines and devices, such as remotely located components, via the network 120.

The network 120 may provide the functionality of a local area network (LAN), a wireless network, a cloud computing environment (e.g., software as a service, platform as a service, infrastructure as a service, etc.), a client-server, a wide area network (WAN), and the like. For example, network 120 may be a LAN or a WAN that may include other systems S1 (138), S2 (140), and S3 (141). Systems S1, S2, and S3 may be identical to image processing device 112 or may be different systems. In some embodiments, one or more systems in network 120 may form a distributed computing/simulation environment that collaboratively performs the embodiments described herein. In some embodiments, one or more systems S1, S2, and S3 may include a CT scanner that obtains CT images (e.g., medical images 146). In addition, network 120 may be connected to Internet 122 to communicate with servers and clients that reside remotely on the internet.

Therefore, network 120 may allow data transmission between the image processing device 112 and a number of various other systems and devices, such as the OIS 128, the radiation therapy device 130, and the image acquisition device 132. Further, data generated by the OIS 128 and/or the image acquisition device 132 may be stored in the memory device 116, the database 124, and/or the hospital database 126. The data may be transmitted/received via network 120, through communication interface 118 in order to be accessed by the processor 114, as required.

The image processing device 112 may communicate with database 124 through network 120 to send/receive a plurality of various types of data stored on database 124. For example, database 124 may include machine data (control points) that includes information associated with a radiation therapy device 130, image acquisition device 132, or other machines relevant to radiotherapy. Machine data information may include control points, such as radiation beam size, arc placement, beam on and off time duration, machine parameters, segments, MLC configuration, gantry speed, MRI pulse sequence, and the like. Database 124 may be a storage device and may be equipped with appropriate database administration software programs. One skilled in the art would appreciate that database 124 may include a plurality of devices located either in a central or a distributed manner.

In some embodiments, database 124 may include a processor-readable storage medium. While the processor-readable storage medium in an embodiment may be a single medium, the term "processor-readable storage medium" should be taken to include a single medium or multiple media (e.g., a centralized or distributed database, and/or associated caches and servers) that store the one or more sets of computer-executable instructions or data. The term "processor-readable storage medium" shall also be taken to include any medium that is capable of storing or encoding a set of instructions for execution by a processor and that cause the processor to perform any one or more of the methodologies of the present disclosure. The term "processor-readable storage medium" shall accordingly be taken to include, but not be limited to, solid-state memories and optical and magnetic media. For example, the processor-readable storage medium may be one or more volatile, non-transitory, or non-volatile tangible computer-readable media.

Image processor 114 may communicate with database 124 to read images into memory device 116 or store images from memory device 116 to database 124. For example, the database 124 may be configured to store a plurality of images (e.g., 3D MRI, 4D MRI, 2D MRI slice images, CT images, 2D Fluoroscopy images, X-ray images, raw data from MR scans or CT scans, Digital Imaging and Communications in Medicine (DIMCOM) data, projection images, graphical aperture images, etc.) that the database 124 received from image acquisition device 132. Database 124 may store data to be used by the image processor 114 when executing software program 144 or when creating radiation therapy treatment plans 142. Database 124 may store the data produced by the trained machine learning mode, such as a neural network including the network parameters constituting the model learned by the network and the resulting estimated data. As referred to herein, "estimate" or "estimated" may be used interchangeably with "predict" or "predicted" and should be understood to have the same meaning. The image processing device 112 may receive the imaging data, such as a medical image 146 (e.g., 2D MRI slice images, CT images, 2D Fluoroscopy images, X-ray images, 3DMRI images, 4D MRI images, projection images, graphical aperture images, image contours, etc.) from the database 124, the radiation therapy device 130 (e.g., an MR-linac), and/or the image acquisition device 132 to generate a treatment plan 142.

In an embodiment, the radiotherapy system 100 may include an image acquisition device 132 that may acquire medical images (e.g., MRI images, 3D MRI, 2D streaming MRI, 4D volumetric MRI, CT images, cone-Beam CT, PET images, functional MRI images (e.g., fMRI, DCE-MRI and diffusion MM), X-ray images, fluoroscopic image, ultrasound images, radiotherapy portal images, SPECT images, and the like) of the patient. Image acquisition device 132 may, for example, be an MRI imaging device, a CT imaging device, a PET imaging device, an ultrasound device, a fluoroscopic device, a SPECT imaging device, or any other suitable medical imaging device for obtaining one or more medical images of the patient. Images acquired by the image acquisition device 132 may be stored within database 124 as either imaging data and/or test data. By way of example, the images acquired by the image acquisition device 132 may be also stored by the image processing device 112 as medical images 146 in memory device 116.

In an embodiment, for example, the image acquisition device 132 may be integrated with the radiation therapy device 130 as a single apparatus (e.g., an MR-linac). Such an MR-linac may be used, for example, to determine a location of a target organ or a target tumor in the patient, so as to direct radiation therapy accurately according to the radiation therapy treatment plan 142 to a predetermined target.

The image acquisition device 132 may be configured to acquire one or more images of the patient's anatomy for a region of interest (e.g., a target organ, a target tumor, or both). Each image, typically a 2D image or slice, may include one or more parameters (e.g., a 2D slice thickness, an orientation, and a location, etc.). In an embodiment, the image acquisition device 132 may acquire a 2D slice in any orientation. For example, an orientation of the 2D slice may include a sagittal orientation, a coronal orientation, or an axial orientation. The processor 114 may adjust one or more parameters, such as the thickness and/or orientation of the 2D slice, to include the target organ and/or target tumor. In an embodiment, 2D slices may be determined from information such as a 3D MRI volume. Such 2D slices may be acquired by the image acquisition device 132 in "real-time" while a patient is undergoing radiation therapy treatment, for example, when using the radiation therapy device 130, with "real-time" meaning acquiring the data in at least milliseconds or less.

The image processing device 112 may generate and store radiation therapy treatment plans 142 for one or more patients. The radiation therapy treatment plans 142 may provide information about a particular radiation dose to be applied to each patient. The radiation therapy treatment plans 142 may also include other radiotherapy information, such as control points including beam angles, gantry angles, beam intensity, dose-histogram-volume information, the number of radiation beams to be used during therapy, the dose per beam, a position of the MLC leaf, information defining a point along an aperture (that may be converted to an MLC leaf position), and the like.

The image processor 114 may generate the radiation therapy treatment plan 142 by using software programs 144 such as treatment planning software (such as Monaco®, manufactured by Elekta AB of Stockholm, Sweden). In order to generate the radiation therapy treatment plans 142, the image processor 114 may communicate with the image acquisition device 132 (e.g., a CT device, an MRI device, a PET device, an X-ray device, an ultrasound device, etc.) to access images of the patient and to delineate a target, such as a tumor, to generate contours of the images. In some embodiments, the delineation of one or more OARs, such as healthy tissue surrounding the tumor or in close proximity to the tumor, may be required. Therefore, segmentation of the OAR may be performed when the OAR is close to the target tumor. In addition, if the target tumor is close to the OAR (e.g., prostate in near proximity to the bladder and rectum), then by segmenting the OAR from the tumor, the radiotherapy system 100 may study the dose distribution not only in the target but also in the OAR.

In order to delineate a target organ or a target tumor from the OAR, medical images, such as MRI images, CT images, PET images, fMRI images, X-ray images, ultrasound images, radiotherapy portal images, SPECT images, and the like, of the patient undergoing radiotherapy may be obtained non-invasively by the image acquisition device 132 to reveal the internal structure of a body part. Based on the information from the medical images, a 3D structure of the relevant anatomical portion may be obtained and used to generate a contour of the image. Contours of the image may include data overlaid on top of the image that delineates one or more structures of the anatomy. In some cases, the contours may be files associated with respective images that specify the coordinates or 2D or 3D locations of various structures of the anatomy depicted in the images.

In addition, during a treatment planning process, many parameters may be taken into consideration to achieve a balance between efficient treatment of the target tumor (e.g., such that the target tumor receives enough radiation dose for an effective therapy) and low irradiation of the OAR(s) (e.g., the OAR(s) receives as low a radiation dose as possible). Other parameters that may be considered include the location of the target organ and the target tumor, the location of the OAR, and the movement of the target in relation to the OAR. For example, the 3D structure may be obtained by contouring the target or contouring the OAR within each 2D layer or slice of an MRI or CT image and combining the contour of each 2D layer or slice. The contour may be generated manually (e.g., by a physician, dosimetrist, or health care worker using a program such as MONACO™ manufactured by Elekta AB of Stockholm, Sweden) or automatically (e.g., using a program such as the Atlas-based auto-segmentation software, ABAS™, manufactured by Elekta AB of Stockholm, Sweden). In certain embodiments, the 3D structure of a target tumor or an OAR may be generated automatically by the treatment planning software.

After the target tumor and the OAR(s) have been located and delineated, a dosimetrist, physician, or healthcare worker may determine a dose of radiation to be applied to the target tumor, as well as any maximum amounts of dose that may be received by the OAR proximate to the tumor (e.g., left and right parotid, optic nerves, eyes, lens, inner ears, spinal cord, brain stem, and the like). After the radiation dose is determined for each anatomical structure (e.g., target tumor, OAR), a process known as inverse planning may be performed to determine one or more treatment plan parameters that would achieve the desired radiation dose distribution. Examples of treatment plan parameters include volume delineation parameters (e.g., which define target volumes, contour sensitive structures, etc.), margins around the target tumor and OARs, beam angle selection, collimator settings, and beam-on times. During the inverse-planning process, the physician may define dose constraint parameters that set bounds on how much radiation an OAR may receive (e.g., defining full dose to the tumor target and zero dose to any OAR; defining 95% of dose to the target tumor; defining that the spinal cord, brain stem, and optic structures receive ≤45Gy, ≤55Gy and <54Gy, respectively). The result of inverse planning may constitute a radiation therapy treatment plan 142 that may be stored in memory device 116 or database 124. Some of these treatment parameters may be correlated. For example, tuning one parameter (e.g., weights for different objectives, such as increasing the dose to the target tumor) in an attempt to change the treatment plan may affect at least one other parameter, which in turn may result in the development of a different treatment plan. Thus, the image processing device 112 may generate a tailored radiation therapy treatment plan 142 having these parameters in order for the radiation therapy device 130 to provide radiotherapy treatment to the patient.

In addition, the radiotherapy system 100 may include a display device 134 and a user interface 136. The display device 134 may include one or more display screens that display medical images, interface information, treatment planning parameters (e.g., projection images, graphical aperture images, contours, dosages, beam angles, etc.) treatment plans, a target, localizing a target and/or tracking a target, or any related information to the user. The user interface 136 may be a keyboard, a keypad, a touch screen or any type of device that a user may use to input information to radiotherapy system 100. Alternatively, the display device 134 and the user interface 136 may be integrated into a device such as a tablet computer (e.g., Apple iPad®, Lenovo Thinkpad®, Samsung Galaxy®, etc.).

Furthermore, any and all components of the radiotherapy system 100 may be implemented as a virtual machine (e.g., VMWare, Hyper-V, and the like). For instance, a virtual machine may be software that functions as hardware. Therefore, a virtual machine may include at least one or more virtual processors, one or more virtual memories, and one or more virtual communication interfaces that together function as hardware. For example, the image processing device 112, the OIS 128, and the image acquisition device 132 could be implemented as a virtual machine. Given the processing power, memory, and computational capability available, the entire radiotherapy system 100 could be implemented as a virtual machine.

Figure 2A:
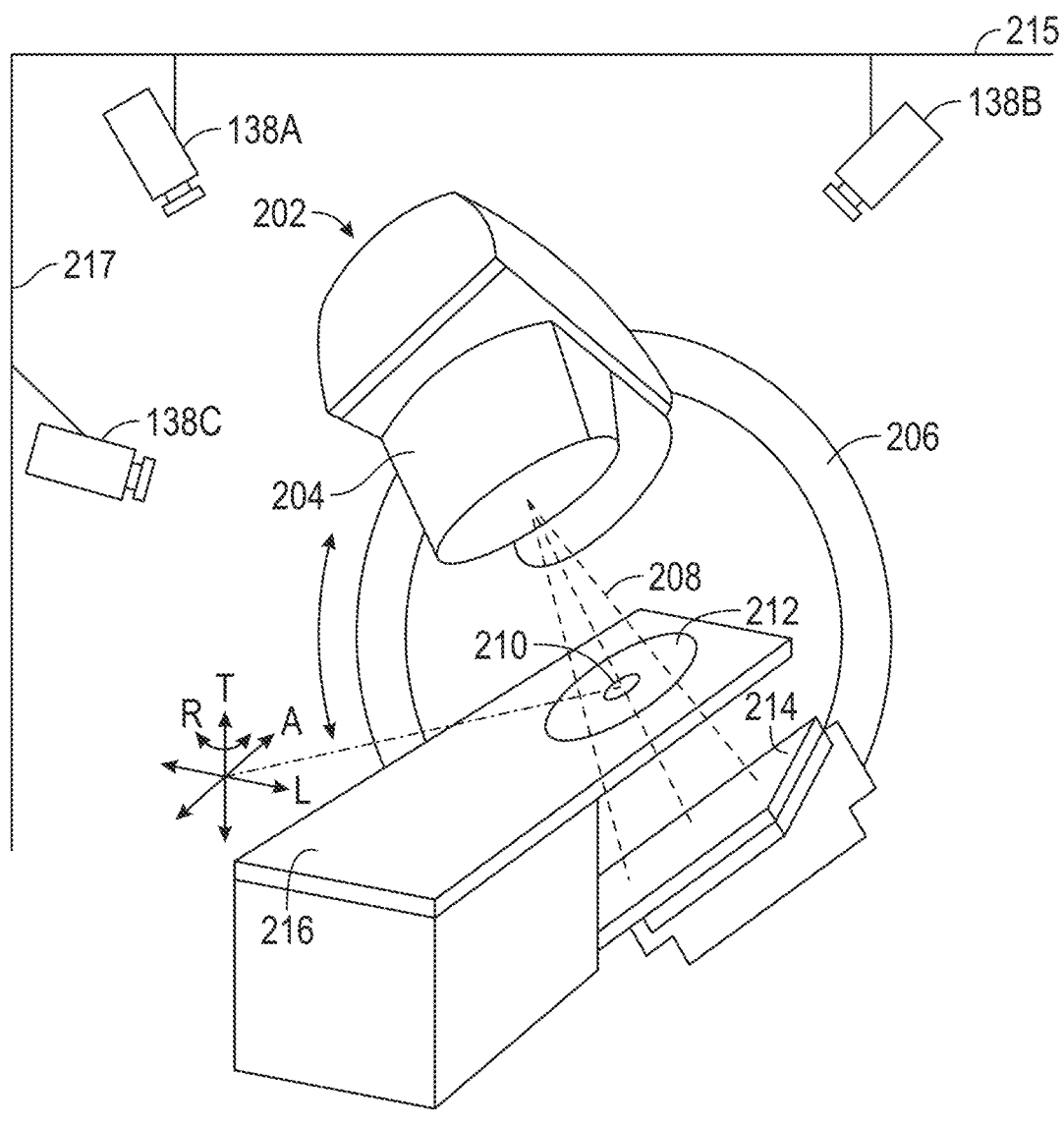
FIG. 2A illustrates an example a radiation therapy system that may include radiation therapy output configured to provide a therapy beam, according to some embodiments of the present disclosure.

FIG. 2A illustrates an example of a radiation therapy device 202 that may include a radiation source, such as an X-ray source or a linear accelerator, a couch 216, an imaging detector 214, and a radiation therapy output 204. The radiation therapy device 202 may be configured to emit a radiation beam 208 to provide therapy to a patient. The radiation therapy output 204 may include one or more attenuators or collimators, such as an MLC as described in the illustrative embodiment of FIG. 5, below.

Referring back to FIG. 2A, a patient may be positioned in a region 212 and supported by the treatment couch 216 to receive a radiation therapy dose, according to a radiation therapy treatment plan. The radiation therapy output 204 may be mounted or attached to a gantry 206 or other mechanical support. One or more chassis motors (not shown) may rotate the gantry 206 and the radiation therapy output 204 around couch 216 when the couch 216 is inserted into the treatment area. In an embodiment, gantry 206 may be continuously rotatable around couch 216 when the couch 216 is inserted into the treatment area. In another embodiment, gantry 206 may rotate to a predetermined position when the couch 216 is inserted into the treatment area. For example, the gantry 206 may be configured to rotate the therapy output 204 around an axis ("A"). Both the couch 216 and the radiation therapy output 204 may be independently moveable to other positions around the patient, such as moveable in transverse direction ("T"), moveable in a lateral direction ("L"), or as rotation about one or more other axes, such as rotation about a transverse axis (indicated as "R"). A controller communicatively connected to one or more actuators (not shown) may control the couch's 216 movements or rotations in order to properly position the patient in or out of the radiation beam 208 according to a radiation therapy treatment plan. Both the couch 216 and the gantry 206 are independently moveable from one another in multiple degrees of freedom, which allows the patient to be positioned such that the radiation beam 208 may precisely target the tumor. The MLC may be integrated and included within gantry 206 to deliver the radiation beam 208 of a certain shape.

The coordinate system (including axes A, T, and L) shown in FIG. 2A may have an origin located at an isocenter 210. The isocenter 210 may be defined as a location where the central axis of the radiation beam 208 intersects the origin of a coordinate axis, such as to deliver a prescribed radiation dose to a location on or within a patient. Alternatively, the isocenter 210 may be defined as a location where the central axis of the radiation beam 208 intersects the patient for various rotational positions of the radiation therapy output 204 as positioned by the gantry 206 around the axis A. As discussed herein, the gantry angle corresponds to the position of gantry 206 relative to axis A, although any other axis or combination of axes may be referenced and used to determine the gantry angle.

Gantry 206 may also have an attached imaging detector 214. The imaging detector 214 is preferably located opposite to the radiation source, and in an embodiment, the imaging detector 214 may be located within a field of the therapy beam 208.

The imaging detector 214 may be mounted on the gantry 206 (preferably opposite the radiation therapy output 204), such as to maintain alignment with the therapy beam 208. The imaging detector 214 rotates about the rotational axis as the gantry 206 rotates. In an embodiment, the imaging detector 214 may be a flat panel detector (e.g., a direct detector or a scintillator detector). In this manner, the imaging detector 214 may be used to monitor the therapy beam 208 or the imaging detector 214 may be used for imaging the patient's anatomy, such as portal imaging (e.g., to provide real X-ray measurements). The control circuitry of radiation therapy device 202 may be integrated within system 100 or remote from it.

In an illustrative embodiment, one or more of the couch 216, the therapy output 204, or the gantry 206 may be automatically positioned, and the therapy output 204 may establish the therapy beam 208 according to a specified dose for a particular therapy delivery instance. A sequence of therapy deliveries may be specified according to a radiation therapy treatment plan, such as using one or more different orientations or locations of the gantry 206, couch 216, or therapy output 204. The therapy deliveries may occur sequentially, but may intersect in a desired therapy locus on or within the patient, such as at the isocenter 210. A prescribed cumulative dose of radiation therapy may thereby be delivered to the therapy locus while damage to tissue near the therapy locus may be reduced or avoided.

In some examples, surface camera imaging data may be acquired using one or more surface cameras 138A-138C. FIG. 2A depicts one non-limiting example in which one or more surface cameras 138A, 138B may be affixed to a ceiling 215 in the therapy treatment room and/or one or more surface cameras 138C may be affixed to a wall 217 in the therapy treatment room. One or more of the surface cameras 138A-138C may acquire surface camera imaging data in real time. The surface camera imaging data from one or more of the surface cameras 138A-138C may then be transmitted to an image processing device, such as to the image processing device 112 of FIG. 1, to generate a model.

Figure 2B:
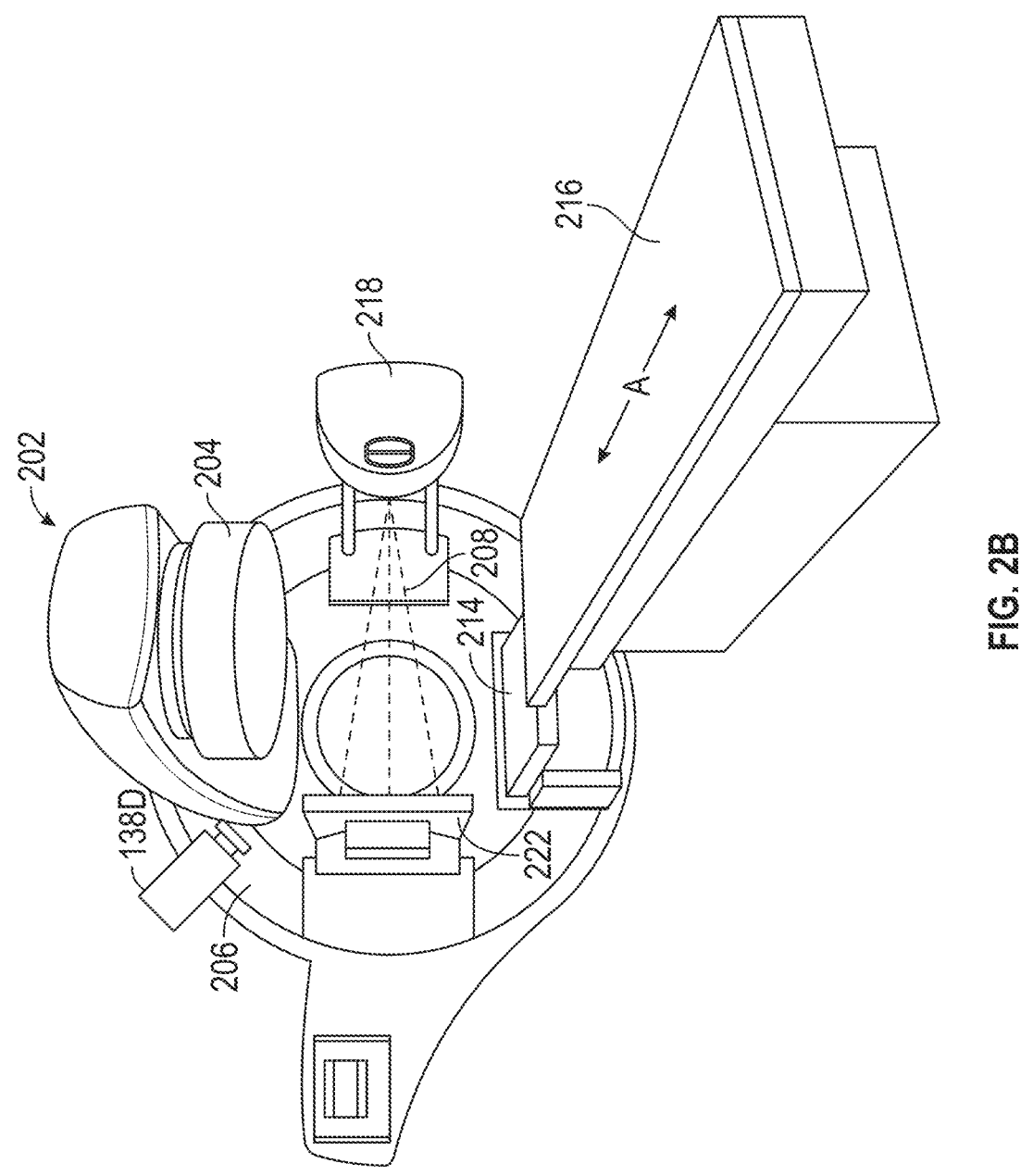
FIG. 2B illustrates an example of a system including a combined radiation therapy system and an imaging system, such as a cone beam computed tomography (CBCT) imaging system, according to some embodiments of the present disclosure.

FIG. 2B illustrates an example of a radiation therapy device 202 that may include a combined linac and an imaging system, such as may include a CT imaging system. The radiation therapy device 202 may include an MLC (not shown). The CT imaging system may include an imaging X-ray source 218, such as providing X-ray energy in a kiloelectron-Volt (keV) energy range which may be used for imaging the patient's anatomy, such as portal imaging (e.g., to provide real X-ray measurements). The imaging X-ray source 218 (also referred to as a "kV source" for kV imaging) may provide a fan-shaped and/or a conical beam 208 directed to an imaging detector 222, such as a flat panel detector. The radiation therapy device 202 may be similar to the system described in relation to FIG. 2A, such as including a radiation therapy output 204, a gantry 206, a couch 216, and another imaging detector 214 (such as a flat panel detector). The X-ray source 218 may provide a comparatively-lower-energy X-ray diagnostic beam, for imaging.

In the illustrative embodiment of FIG. 2B, the radiation therapy output 204, e.g., MV source, and the X-ray source 218, e.g., kV source, may be mounted on the same rotating gantry 206, rotationally-separated from each other by 90 degrees. This arrangement may enable imaging perpendicular to the beam of radiation output by radiation therapy output 204, which, in some embodiments, may be a Megavolt (MV) treatment beam. The kV source 218 may be used to acquire 2D X-ray projections for kV imaging as the kV source 218 moves around the patient along gantry 206.

In another embodiment, two or more X-ray sources may be mounted along the circumference of the gantry 206, such as each having its own detector arrangement to provide multiple angles of diagnostic imaging concurrently. Similarly, multiple radiation therapy outputs 204 may be provided.

FIG. 2B depicts another non-limiting example in which one or more surface cameras 138D may acquire surface camera imaging data. In the example shown in FIG. 2B, a surface camera 138D may be affixed to a frontside of a radiation therapy device 202, such as to a frontside of a CT bore and another surface camera may be affixed to a backside of the radiation therapy device 202, such as to a backside of a CT bore. In this manner, the surface cameras may provide a continuous view of the patient. The surface camera imaging data from the surface cameras, such as the surface camera 138D and a backside surface camera may then be transmitted to an image processing device, such as to the image processing device 112 of FIG. 1, to generate a model.

Figure 3:
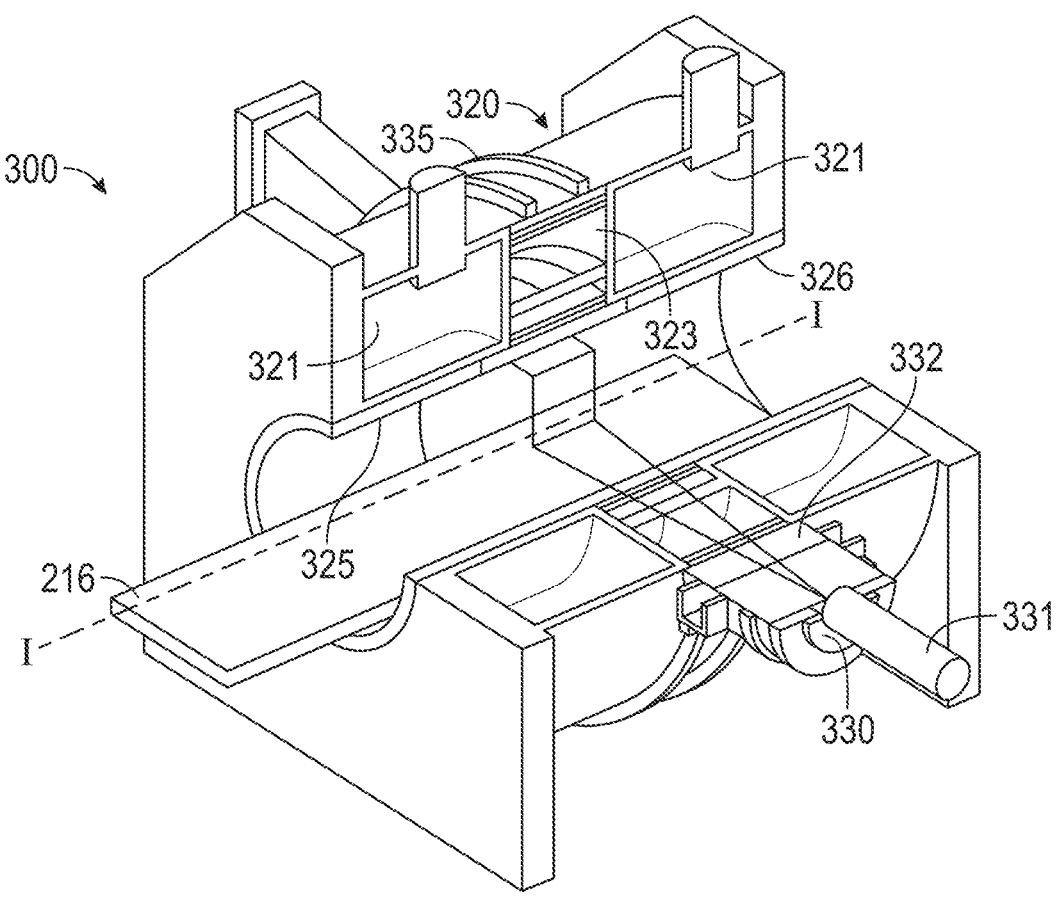
FIG. 3 illustrates a partially cut-away view of an example system including a combined radiation therapy system and an imaging system, such as a nuclear MR imaging (MM) system, according to some embodiments of the present disclosure.
Figure 4B:
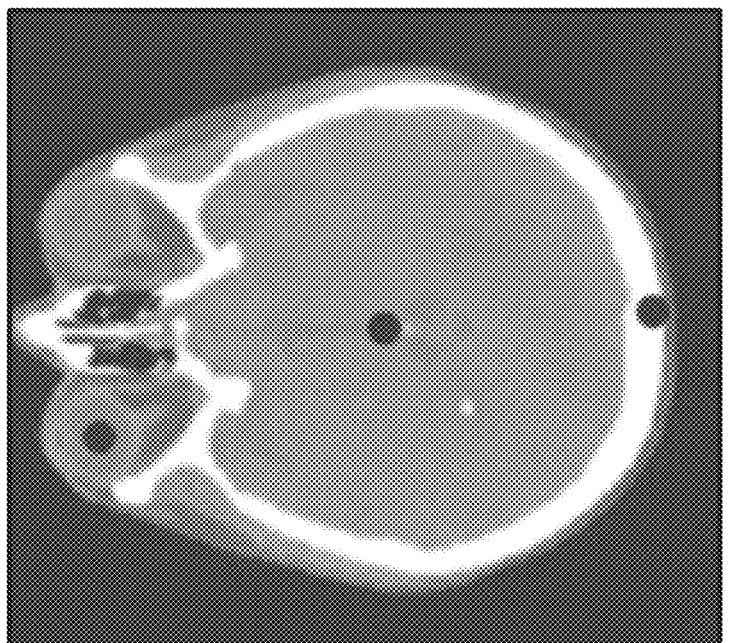
FIGS. 4A and 4B depict the differences between an example MRI image and a corresponding CT image, respectively, according to some embodiments of the present disclosure.
Figure 4A:
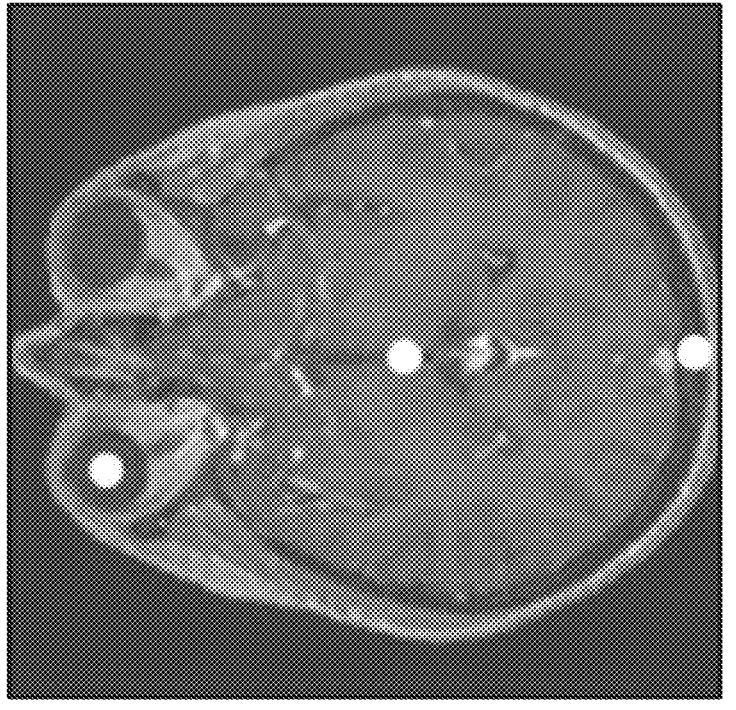

FIG. 3 depicts an example radiation therapy system 300 that may include combining a radiation therapy device 202 and an imaging system, such as a nuclear MR imaging system (e.g., known in the art as an MR-linac) consistent with the disclosed embodiments. As shown, system 300 may include a couch 216, an image acquisition device 320, and a radiation delivery device 330. System 300 delivers radiation therapy to a patient in accordance with a radiotherapy treatment plan. In some embodiments, image acquisition device 320 may correspond to image acquisition device 132 in FIG. 1 that may acquire origin images of a first modality (e.g., MRI image shown in FIG. 4A) or destination images of a second modality (e.g., CT image shown in FIG. 4B).

Couch 216 may support a patient (not shown) during a treatment session. In some implementations, couch 216 may move along a horizontal translation axis (labelled "I"), such that couch 216 may move the patient resting on couch 216 into and/or out of system 300. Couch 216 may also rotate around a central vertical axis of rotation, transverse to the translation axis. To allow such movement or rotation, couch 216 may have motors (not shown) enabling the couch 216 to move in various directions and to rotate along various axes. A controller (not shown) may control these movements or rotations in order to properly position the patient according to a treatment plan.

In some embodiments, image acquisition device 320 may include an MRI machine used to acquire 2D or 3D MRI images of the patient before, during, and/or after a treatment session. Image acquisition device 320 may include a magnet 321 for generating a primary magnetic field for magnetic resonance imaging. The magnetic field lines generated by operation of magnet 321 may run substantially parallel to the central translation axis I. Magnet 321 may include one or more coils with an axis that runs parallel to the translation axis I. In some embodiments, the one or more coils in magnet 321 may be spaced such that a central window 323 of magnet 321 is free of coils. In other embodiments, the coils in magnet 321 may be thin enough or of a reduced density such that they are substantially transparent to radiation of the wavelength generated by radiotherapy device 330. Image acquisition device 320 may also include one or more shielding coils, which may generate a magnetic field outside magnet 321 of approximately equal magnitude and opposite polarity in order to cancel or reduce any magnetic field outside of magnet 321. As described below, radiation source 331 of radiotherapy device 330 may be positioned in the region where the magnetic field is cancelled, at least to a first order, or reduced.

Image acquisition device 320 may also include two gradient coils 325 and 326, which may generate a gradient magnetic field that is superposed on the primary magnetic field. Coils 325 and 326 may generate a gradient in the resultant magnetic field that allows spatial encoding of the protons so that their position may be determined. Gradient coils 325 and 326 may be positioned around a common central axis with the magnet 321 and may be displaced along that central axis. The displacement may create a gap, or window, between coils 325 and 326. In embodiments where magnet 321 may also include a central window 323 between coils, the two windows may be aligned with each other.

In some embodiments, image acquisition device 320 may be an imaging device other than an MRI, such as an X-ray, a CT, a CBCT, a spiral CT, a PET, a SPECT, an optical tomography, a fluorescence imaging, ultrasound imaging, radiotherapy portal imaging device, or the like. As would be recognized by one of ordinary skill in the art, the above description of image acquisition device 320 concerns certain embodiments and is not intended to be limiting.

Radiotherapy device 330 may include the radiation source 331, such as an X-ray source or a linac, and an MLC 332 (shown below in FIG. 5). Radiotherapy device 330 may be mounted on a chassis 335. One or more chassis motors (not shown) may rotate chassis 335 around couch 216 when couch 216 is inserted into the treatment area. In an embodiment, chassis 335 may be continuously rotatable around couch 216 when couch 216 is inserted into the treatment area. Chassis 335 may also have an attached radiation detector (not shown), preferably located opposite to radiation source 331 and with the rotational axis of chassis 335 positioned between radiation source 331 and the detector. Further, device 330 may include control circuitry (not shown) used to control, for example, one or more of couch 216, image acquisition device 320, and radiotherapy device 330. The control circuitry of radiotherapy device 330 may be integrated within system 300 or remote from it.

During a radiotherapy treatment session, a patient may be positioned on couch 216. System 300 may then move couch 216 into the treatment area defined by magnet 321, coils 325 and 326, and chassis 335. Control circuitry may then control radiation source 331, MLC 332, and the chassis motor(s) to deliver radiation to the patient through the window between coils 325 and 326 according to a radiotherapy treatment plan.

FIG. 2A, FIG. 2B, and FIG. 3 illustrate generally embodiments of a radiation therapy device configured to provide radiotherapy treatment to a patient, including a configuration where a radiation therapy output may be rotated around a central axis (e.g., an axis "A"). Other radiation therapy output configurations may be used. For example, a radiation therapy output may be mounted to a robotic arm or manipulator having multiple degrees of freedom. In yet another embodiment, the therapy output may be fixed, such as located in a region laterally separated from the patient, and a platform supporting the patient may be used to align a radiation therapy isocenter with a specified target locus within the patient.

As discussed above, radiation therapy devices described by FIG. 2A, FIG. 2B, and FIG. 3 include an MLC for shaping, directing, or modulating an intensity of a radiation therapy beam to the specified target locus within the patient.

Figure 5:
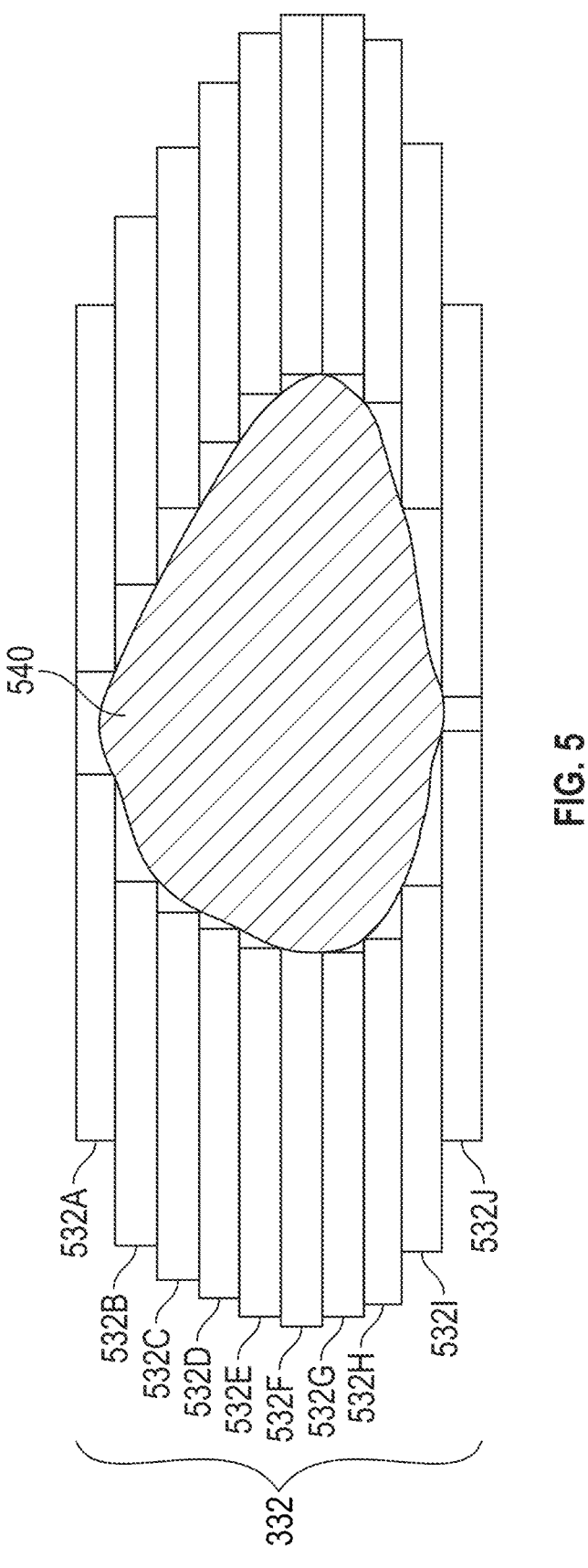
FIG. 5 illustrates an example of a collimator configuration for shaping, directing, or modulating an intensity of a radiation therapy beam, according to some embodiments of the present disclosure.

FIG. 5 illustrates an example of an MLC 332 that includes leaves 532A through 532J that may be automatically positioned to define an aperture approximating a tumor 540 cross section or projection. The leaves 532A through 532J permit modulation of the radiation therapy beam. The leaves 532A through 532J may be made of a material specified to attenuate or block the radiation beam in regions other than the aperture, in accordance with the radiation treatment plan. For example, the leaves 532A through 532J may include metallic plates, such as comprising tungsten, with a long axis of the plates oriented parallel to a beam direction and having ends oriented orthogonally to the beam direction (as shown in the plane of the illustration of FIG. 2A). A "state" of the MLC 332 may be adjusted adaptively during a course of radiation therapy treatment, such as to establish a therapy beam that better approximates a shape or location of the tumor 540 or another target locus. This is in comparison to using a static collimator configuration or as compared to using an MLC 332 configuration determined exclusively using an "offline" therapy planning technique. A radiation therapy technique using the MLC 332 to produce a specified radiation dose distribution to a tumor or to specific areas within a tumor may be referred to as IMRT.

Figure 6:
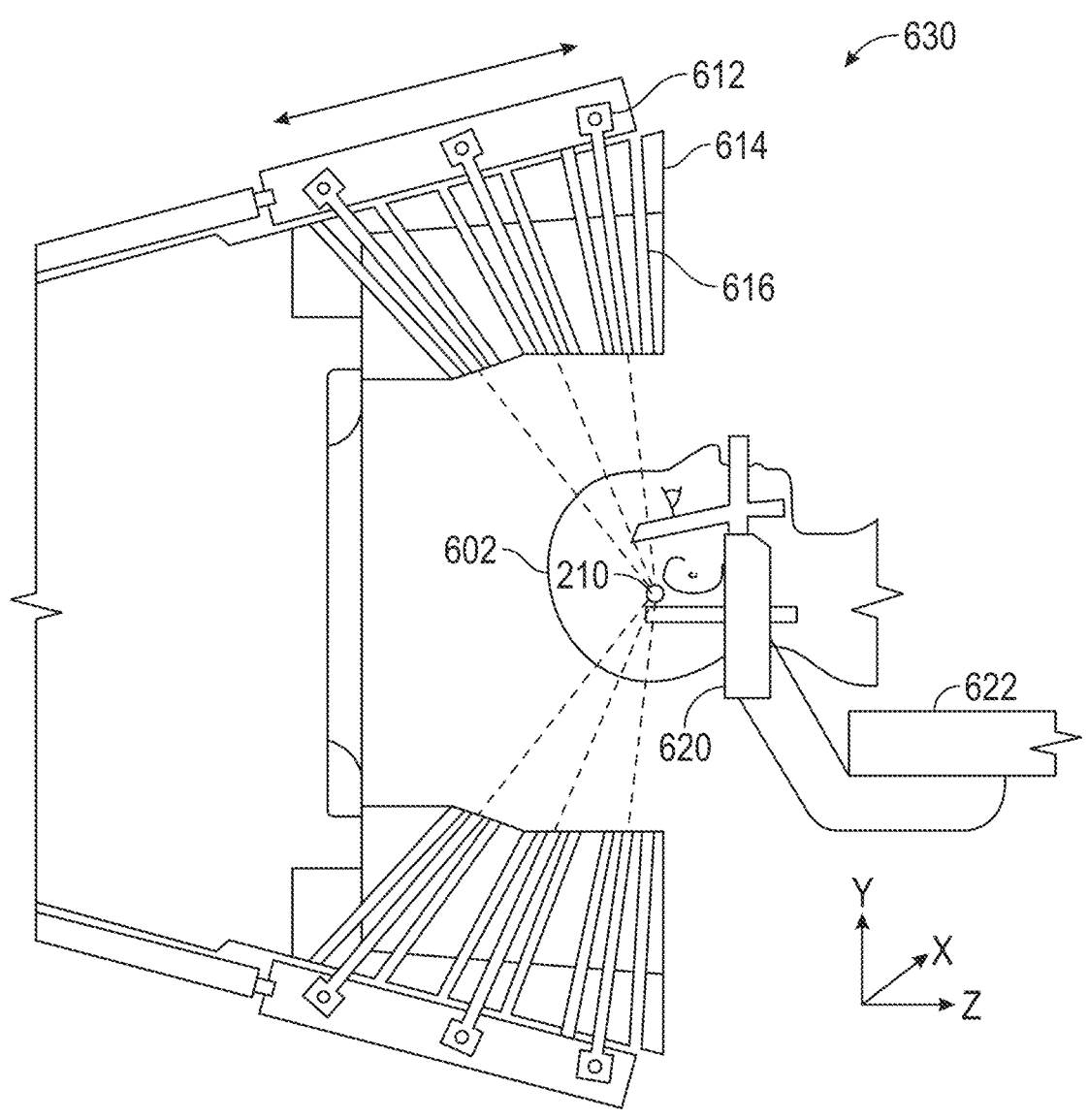
FIG. 6 illustrates an example of a Gamma Knife radiation therapy system, according to some embodiments of the present disclosure.

FIG. 6 illustrates an embodiment of another type of radiotherapy device 630 (e.g., a Leksell Gamma Knife), according to some embodiments of the present disclosure. As shown in FIG. 6, in a radiotherapy treatment session, a patient 602 may wear a coordinate frame 620 to keep stable the patient's body part (e.g., the head) undergoing surgery or radiotherapy. Coordinate frame 620 and a patient positioning system 622 may establish a spatial coordinate system, which may be used while imaging a patient or during radiation surgery. Radiotherapy device 630 may include a protective housing 614 to enclose a plurality of radiation sources 612. Radiation sources 612 may generate a plurality of radiation beams (e.g., beamlets) through beam channels 616. The plurality of radiation beams may be configured to focus on an isocenter 210 from different directions. While each individual radiation beam may have a relatively low intensity, isocenter 210 may receive a relatively high level of radiation when multiple doses from different radiation beams accumulate at isocenter 210. In certain embodiments, isocenter 210 may correspond to a target under surgery or treatment, such as a tumor.

After initial images of the target are acquired, the location and/or orientation of the target region may change. For example, the patient may shift during transfer to the treatment room, during movement within the treatment room (e.g., positioning on a couch, bed, or table), or during the administration of radiotherapy. For example, a patient may have voluntarily or involuntarily movements due to regular biological processes, including, e.g., breathing, swallowing, blinking, twitching, peristalsis, digestion, beating of the heart, coughing, passing gas, or other movements.

Additionally, tracking anatomy across different radiation therapy treatment sessions (also referred to as fractions) may be complicated, because a patient may lose or gain weight between each fraction, a target region (e.g., tumor) may change size (e.g., shrink or get larger), or the anatomy around the target region may affect the position of the target region (e.g., the volume of a patient's bladder may change across fractions, affecting the location of surrounding structures).

These fraction-to-fraction changes in the location and/or orientation of the target region may reduce the efficacy of radiotherapy. For example, if the actual orientation or location of the target region is different than the assumed orientation or location based on prior imaging and/or inaccurate alignment with prior imaging, then the correct dose of radiation may not be delivered to the intended target region. Additionally, surrounding healthy structures may receive radiation instead of, or in addition to, the intended target region. Exposing the wrong area to radiation may ultimately harm or kill surrounding healthy cells. Further, it may be desirable to match images of the patient's anatomical structures taken across fractions and/or to an original image taken of the patient to track the location of dose delivery and the overall dose delivered to the patient.

Using various techniques of this disclosure, a system, such as the radiotherapy system 100 of FIG. 1, may adapt a reference radiotherapy treatment plan having a plurality of control points during a radiotherapy treatment session. The system may obtain treatment imaging data of the subject during the radiotherapy treatment session and one or more parameters may be determined using the treatment imaging data. Then, the system may generate a current radiotherapy treatment plan based on the parameter(s). The system may modify the reference radiotherapy treatment plan for the radiotherapy treatment session during the radiotherapy treatment session by updating one of the plurality of control points of the reference radiotherapy treatment plan with a control point of a current radiotherapy treatment plan. An aspect of this disclosure is to define a set of parameters $q=[q_1, q_2, \ldots, q_J]$ that governs the degrees of freedom of the patient anatomy during treatment. The system may define a parametric function Q that maps a reference image $I_{ref}$ into a new image I, i.e., $I=Q(I_{ref}; q)$. In this manner, the instantaneous state of the patient's anatomy may be uniquely specified through knowledge of the parameters q. The system does not know a priori what these parameters are at any given time point $t_i$ during treatment, but if we did, we would know the image $I_i$.

At each time point $t_i$, the system may acquire patient measurements $M_i$ that the system may use to calculate the parameters $q_i$. Measurements may be acquired with, for example, a kV imager affixed to the linear accelerator, 2D MR slices, a surface camera, or the treatment beam itself (MV imager). Examples of methods to calculate real-time evolving 3D images from intrafractional imaging data; either using 2D MR slices on an MR linac, or kV imaging, optionally in combination with surface camera data, on a conventional linac are described in US2020129780, US20170360325, US20200129784, US20200160972, and U.S. Provisional Application No. 62/991,356, filed Mar. 18, 2020, each of which is incorporated by reference herein, its entirety.

The measurement geometry $G_i$ may change with time. For example, a kV imaging angle may rotate about the patient as the treatment progresses (because it is affixed to the linac gantry), or an MR slice may alternate between sagittal and coronal directions. The system may define T as a function that generates the parameters $q_i$ from patient measurements $M_i$ for a given measurement geometry $G_i$ i.e., $q_i=T(M_i, G_i)$. Once the system defines the function T, the system may determine the evolving patient image $I_i$ directly from patient measurements $M_i$ through $I_i=Q(I_{ref}; q_i)$.

The system may define V as a function that adapts an initial structure set $S_{ref}$ defined on image $I_{ref}$ to a new structure set $S_i$ defined on image $I_i$, for given parameters $q_i$ i.e., $S_i=V(S_{ref}; q_i)$. The system may define R as a function that adapts the initial reference plan $P_{ref}$ to a new plan $P_i$, i.e., $P_i=R(P_{ref}; q_i)$. The plan may include control points $$P_i = \{A_1^i, A_2^i, \ldots, A_M^i\}.$$

In some embodiments, it is expected that R is such that $$A_m^i$$

is similar to $$A_m^{ref}$$

This is a soft requirement but may be useful for two reasons: a) it may minimize MLC leaf travel to switch 'on the fly' between $$A_m^{ref}$$

and $$A_m^i,$$

and b) it may reduce the chance of deviating too far away from the initial plan, thus reducing the risk of errors in real-time adaptation.

To summarize: at each time point $t_i$ during beam-on, the radiotherapy system may measure $M_i$ under geometry $G_i$. The system may then calculate the vector of parameters $q_i=T(M_i, G_i)$; calculate the plan $P_i=R(P_{ref}; q_i)$, which has control points $$\{A_m^i\};$$

and replace the current control point $$A_m^{ref}$$

with $$A_m^i$$

where m is the label for the currently delivered control point. Although not needed to generate the plan, in some embodiments the system may also calculate the instantaneous patient image $I_i=Q(I_{ref}; q_i)$ and structure set $S_i=V(S_{ref}; q_i)$ as well as calculate the dose distribution $D_i$ on this image and/or dose-volume histograms on the structure set resulting from plan $P_i$.

Described below are some examples of how to generate the functions Q, S and R.

Generation of Q

The function Q defines the range of expected variations in patient image I, given an initial reference image $I_{ref}$. The function Q may be defined, for example, by a biomechanical patient model, or by a deep learning algorithm trained over a large number of patient datasets. In some embodiments, the system may acquire multiple 3D images for the patient under treatment, calculate deformation vector fields (DVFs) between those images, and reduce the dimensionality of the resulting DVFs so that they may be fully defined by a small number of parameters. When adapting plans to compensate for respiratory motion, the aforementioned multiple 3D images may be efficiently acquired with a respiratory-binned 4D scan, such as a 4D CBCT or 4D MRI. Each respiratory phase may be represented by a 3D image $I_p$. An image from one of the phases may be defined as the reference image $I_{ref}$ or alternatively, a composite reference image, such as a mid-position image, may be used.

First, the system may use deformable image registration (DIR) to find a deformation vector field (DVF) between the reference image $I_{ref}$ and each of the images for the other phases $I_p$, such that $$I_p(r) = I_{ref}(r - DVF_p(r))$$

where r is a 3D position vector. Then, the system may perform a principal component analysis (PCA) to decompose the DVF into a set of principal components. Typically, for respiratory variations within a treatment session, two or three PCA components are sufficient to describe the DVF. Any DVF may then be expressed in terms of its principal components as $$DVF(r) = \sum_{i=1}^{I} q_i DVF^{(i)}(r)$$

The function Q may then be defined as $$Q(I_{ref}; q) = I_{ref}(r - q \cdot DVF(r))$$

where $$DVF(r) = \left( DVF^{(1)}(r), \ldots, DVF^{(I)}(r) \right)^T.$$

It is not necessary that the analysis use DVFs; it may use image intensities directly, for example, or any method that may be used to map one image to another.

Generation of T

The goal of the function T is to find the parameters $q_i$ from a measurement $M_i$ under measurement geometry $G_i$. This may be done in different ways.

Example 1

The system may select multiple samples of q over the expected range that would be expected during a treatment session. For example, the samples may be selected based on a grid, or random sampling over a range of expected values. For each sampled q, the system may generate the corresponding image I using the previously generated function Q, and for each expected measurement geometry G, the system may simulate a measurement M from the image I. This measurement simulation may, for example, be carried out by extracting a slice from image I at a given position and orientation in the case of 2D MM slices, by ray-tracing projections through image I in the case of x-ray imaging, or even by more accurately simulate projections using a Monte Carlo simulation or Boltzmann solver to generate projections from the physics of radiation transport through the image I. Optionally, the system may reduce the dimensionality of the simulated measurements. This may be done for example by a PCA analysis of the measurements, a PCA analysis of the 2D DVF between the measurement and a reference measurement, feature extraction and/or patch selection. This disclosure refers to measurements as $M_i$ regardless of whether they have been reduced in dimensionality or not. The system may then calculate a regression between the measurements and q resulting in q=T(M, G). For example, the regression may be a simple nearest-neighbor, linear, or polynomial regression, or may be calculated from machine learning principles such as random forest regression, support vector regression, or neural network regression. Note that the regression may be repeated for each measurement geometry G.

Example 2

In some cases, it may be desirable to first estimate the image I directly from the measurements M and then extract the parameters q from the image rather than from the measurements. In the case of 2D x-ray projections, for example, the system may execute an algorithm to reconstruct an image from a single projection, such as by training a deep learning model or by aligning/deforming previous projections to the current time and using them to reconstruct a full image. Once the system has the full image I, the system may calculate the parameters q. For example, the system may use the regression method of Example 1, replacing measurements with images.

Example 3

In some cases, the system may evaluate the function T directly each time it is needed using an optimization algorithm. The system may execute an algorithm that may iteratively vary the parameters, simulate what a measurement would like with those parameters, compare to the actual measurement using a metric, and continue to try to improve on this comparison by iteratively modifying the parameters until an 'optimal' value of the metric is achieved. This process may be computationally expensive, however. An alternative to this example is to first calculate images I directly from the measurements M (as in Example 2) and then finding the optimal values of q that will generate this image (or its DVF) using an optimization algorithm.

Generation of V

The goal of the function V is to find the structure set $S_i$ for a given patient image $I_1$ represented by parameters $q_i$. In some embodiments, the structure set may be found by an auto-contouring algorithm. In others, if the function Q used to determine $I_i$ is based on a DVF approach, then this same DVF may be used to deform the reference structure set $S_{ref}$ onto $S_i$.

Generation of R

The goal of the function R is to find the optimal plan $P_i$ with control points $$A_m^i$$

for a given deformable patient image $I_i$ and structure set $S_i$ represented by parameters $q_i$.

In some examples, the system may generate multiple samples of q, in an analogous fashion as described in the generation of T (Example 1). In some examples, if Example 1 is used for the generation of S, this process may be done concurrently.

For each sample of $q=q_p$, the system may generate an image $I_p$ and a structure set $S_p$ using the previously generated functions Q and V, and use these to generate a treatment plan Pp using a treatment planning algorithm. The system may then use these data pairs $[q_p, P_p]$ to train the function R that maps q to P, i.e., $P=R(P_{ref}; q)$.

When generating these treatment plans $P_p$, it may be desirable to enforce a consistency between the corresponding control points $$A_m^p.$$

There are different ways that this may be achieved. One way is to simultaneously optimize the plans $P_p$ over all images $I_p$, with an objective function that penalizes differences between corresponding control $$A_m^p$$

of the same index m. Another is to use a warm start optimization to adapt the plan ref to each $I_p$. Warm start optimization starts with the reference plan and re-optimizes to the new image, keeping the same number of control points. It essentially modifies the apertures and weights, and generally tends to modify them only as needed to adapt to the new image. In some embodiments the warm start optimization may be used in combination with a virtual couch shift algorithm.

Once the system has generated the data pairs $[q_p, P_p]$, the system may perform a regression that determines the function R. In some examples, the system may first perform a dimensionality reduction on the plans $P_p$. For example, the system may calculate 2D DVFs or MLC translation vectors between the $$A_m^{ref}$$

and $$A_m^p$$

for each corresponding aperture, and then the system may use a PCA analysis to reduce the dimensionality to a few parameters. The system may use these parameters to represent the plans $P_p$ in the regression, which may greatly simplify the complexity of the task.

In this manner, by generating $q_i$ through measurements $M_i$ at each time point during treatment, the system may evaluate the plan $P_i$ from the trained R and then select the appropriate control point from this plan to replace the initially scheduled control point.

In some examples, the plans $P_i$ generated from the function R are further refined by the system to better conform to target and/or organs-at-risk. For example, the system may use a segment-aperture morphing algorithm (SAM) for this purpose.

To summarize, using the techniques of this disclosure, a system, such as the radiotherapy system 100 of FIG. 1, may acquire patient measurements $M_i$ that the system may use to calculate the parameters $q_i$. Using the parameters $q_i$, the system may determine new plans $P_i$ and interchange previously scheduled control points with newly generated control points.

To do this, the system may use a first model that relates the patient measurements $M_i$ to the parameters $q_i$. To build the first model, e.g., which may occur in a training phase, the system may acquire imaging data (e.g., a 4D imaging data set), determine DVFs between respiration phases, and perform a PCA analysis to determine the parameters $q_i$. The system may then generate simulated images using the parameters $q_i$ and extract or simulate different measurements $M_i$ from those simulated images. The system may then build a regression model between the measurements $M_i$ and the parameters $q_i$ so that whenever the system has a measurement $M_i$, it may calculate the parameter $q_i$. In addition, the system may build a second model, e.g., which may occur in a training phase, that relates the parameters $q_i$ and the plans $P_i$, e.g., the control points of the plans.

FIG. 7 illustrates a flow diagram of an example of a computer-implemented method for adaptation of a reference radiotherapy treatment plan having a plurality of control points, performed on a subject in a radiotherapy treatment session, according to some embodiments of the present disclosure. The method 700 is represented as a set of blocks 702-708 that describe operations of the method. The method may be embodied in a set of instructions stored in at least one computer-readable storage device of a computing device (s). A computer-readable storage device excludes transitory signals. In contrast, a signal-bearing medium may include such transitory signals. A machine-readable medium may be a computer-readable storage device or a signal-bearing medium. The computing device(s) may have one or more processors that execute the set of instructions to configure the one or more processors to perform the operations illustrated in FIG. 7. The one or more processors may instruct other components of the computing device(s) to carry out the set of instructions. For example, the computing device may instruct a network device to transmit data to another computing device or the computing device may provide data over a display interface to present a user interface. In some examples, performance of the method may be split across multiple computing devices using a shared computing infrastructure.

At operation 702, a radiation therapy system, such as the radiation therapy system 100 shown in FIG. 1, may obtain treatment imaging data of the subject during the radiotherapy treatment session. For example, the radiation therapy system may obtain treatment imaging data using an image acquisition device, such as the image acquisition device 132 of FIG. 1. The image acquisition device may acquire treatment imaging data such as by using a kV imager affixed to the linear accelerator, 2D MR slices, a surface camera, or the treatment beam itself (MV imager). In other words, the radiation therapy system may obtain the treatment imaging data of the subject during the radiotherapy treatment session using at least one of a kV imaging data, 2D MR slices, surface camera imaging data, cone-beam CT (CBCT) imaging data, or MV imaging data.

At operation 704, the radiation therapy system, e.g., the processor 112 of the radiation therapy system 100 of FIG. 1, may determine at least one parameter using the treatment imaging data. For example, the radiation therapy system may determine one or more parameters q, such as PCA components, that may represent a motion of the patient.

At operation 706, the radiation therapy system, e.g., the processor 112 of the radiation therapy system 100 of FIG. 1, may generate a current radiotherapy treatment plan based on the at least one parameter. For example, the radiation therapy system may generate a current radiotherapy plan having a first plurality of control points that is different from the reference radiotherapy treatment plan having a second plurality of control points. For example, the radiation therapy system may adapt one or more control points, e.g., a sequence of gantry angles, aperture leaf positions, and/or intensity weights, based on the one or more parameters q that may represent the motion of the patient.

At operation 708, the radiation therapy system, e.g., the processor 112 of the radiation therapy system 100 of FIG. 1, may modify the reference radiotherapy treatment plan for the radiotherapy treatment session during the radiotherapy treatment session by updating one of the plurality of control points of the reference radiotherapy treatment plan with a control point of the current radiotherapy treatment plan. In some examples, an individual one of the control points includes aperture information, such as a number of (x, y) coordinates representing vertices of an aperture shape. In some examples, an individual one of the control points includes multi-leaf collimator leaf position information. In some examples, an individual one of the control points includes dose rate information related to the delivery of the radiation dosage to the subject. Dose rate information may include monitor units, which is a relative measure proportional to dose rate that is used by linacs.

In some examples, the radiation therapy system may generate a current image of the subject using the one or more parameters q and a reference image. It should be noted that the reference image need not be generated from the treatment imaging data. In some such examples, the radiation therapy system may then generate a current structure set of the subject using the at least one parameter and a reference structure set. In some examples, the radiation therapy system may generate a current dose distribution using the current radiotherapy treatment plan and the current image. In some such examples, the radiation therapy system may generate a dose volume histogram using the current dose distribution and the current structure set.

In some examples, the radiation therapy system may perform a training phase. For example, the radiation therapy system may generate at least two training images representing potential anatomical states, e.g., anatomical positions, of the subject, the at least two training images corresponding to at least two training parameters. Then, the radiation therapy system may generate at least two training radiotherapy treatment plans corresponding to the at least two training images. The radiation therapy system may generate a training regression between the at least two training parameters and the at least two training treatment plans.

By way of a non-limiting example of purposes of explanation only, the radiation therapy system may generate at least two reference images of the subject. For example, the radiation therapy system may generate a 4D CBCT image of the patient, such as at least two reference images of the patient, such as ten sequential reference images, e.g., 3D images, to represent a typical respiratory cycle of the patient. In other words, the radiation therapy system may generate a 3D image that moves in time.

The radiation therapy system may select one of the reference images as a primary reference image. For example, the radiation therapy system may select one of the 3D images as a primary reference image, such as one 3D image of the ten 3D images. Then, the radiation therapy system may generate a DVF between the primary reference image and each of the other reference images. For example, the radiation therapy system may generate DVFs for each pixel (or voxel) between the selected primary reference 3D image and the remaining nine 3D images, which results in ten DVFs, for example.

The radiation therapy system may then apply a dimensionality reduction technique to the DVFs. For example, the radiation therapy system may perform a PCA to reduce the DVFs to at least two parameters q, e.g., training parameters q. Application of PCA to the DVFs results in a set of principal components or coefficients that define vectors. A principal component is given by a linear combination of variables and principal component weights associated with those variables. Then, using a predefined criterion, such as a predefined amount of variability, or a predefined desired accuracy of a reconstructed deformation field, the radiation therapy system may reduce the dimensionality by selecting one or more PCA components from the set of principal components.

The radiation therapy system may quantify the motion of the patient in terms of those two or more parameters. That is, by knowing those two or more parameters, the radiation therapy system may determine an associated DVF, and warp the primary reference image to a new image.

Dimensionality reduction techniques are not limited to the use of PCA. Other non-limiting examples of dimensionality reduction techniques include independent component analysis (ICA), kernel PCA, canonical correlation analysis, locally linear embedding (LLE), Hessian LLE, Laplacian eigenmaps, local tangent space alignment, maximum variance unfolding, and maximally informative dimensions.

Using the two or more parameters, the radiation therapy system may select combinations of the parameters and build at least two training images representing potential anatomical states of the subject, e.g., at least two different possibilities of patient positioning. For example, the radiation therapy system may generate 100 patient images. Then, the radiation therapy system may generate a training radiotherapy treatment plan for each of those patient images, e.g., 100 training radiotherapy treatment plans corresponding to the 100 patient images. At this point, the radiation therapy system has the first image that is associated with a reference treatment plan and may adapt that plan to the 100 images that were generated, such as using warm startup optimization.

Next, the radiation therapy system may determine a relationship between the control points corresponding to the images and the parameters. In this manner, the parameters control the images and the control points of each of the treatment plans. For example, by changing the parameters q1 and q2, the radiation therapy system may modify the control points for each treatment plan.

Individual control points may be an aperture, for example. The aperture may change depending on which images the radiation therapy system is analyzing. The radiation therapy system may calculate a DVF, for example, between one aperture and the next, determine the deformations of the apertures, and then perform a PCA based on the deformations of those apertures to determine at least two parameters that describe the deformation of the apertures. In other words, during the treatment, when an image is generated, the radiation therapy system may determine the parameters and, using those parameters, determine how the aperture will change, for example, based on the motion of the patient. Then, using a training regression, the radiation therapy system may determine a relationship between the parameters of the apertures and the parameters q of the patient image. Once the radiation therapy system has determined that relationship, the radiation therapy system may determine the patient motion parameters q, calculate aperture deformation parameters, for example, and then modify the beam.

In some examples in which the radiation therapy system generates the current radiotherapy treatment plan based on at least one parameter may, the radiation therapy system may generate, using the training regression, the current radiotherapy treatment plan from the at least one parameter.

In some examples in which the radiation therapy system generates at least two training treatment plans corresponding to the at least two training images, the radiation therapy system may modify the reference radiotherapy treatment plan to the at least two training images using a segment-aperture morphing algorithm.

In some examples in which the radiation therapy system generates at least two training images, the radiation therapy system may generate at least two deformation vector fields using one or more principal components and at least one principal component weights, and generate the at least two training images by deforming the primary reference image using the at least one deformation vector fields and the at least one weight. For example, if a principal component model was determined in a training phase, as previously described, then the principal component weights may, for example, be uniformly or randomly sampled multiple times. The sampled weights may then be used to determine a weighted sum of each of the principal components, This process results in many potential deformation vector fields that the patient may undergo. Each of these may be used to deform the reference image, leading to many potential images that could represent the patient at any given time. It should be noted that in some examples, the principal component weights are the parameters q of the patient image.

In some examples, the radiation therapy system may determine the at least one parameter by using a principal component model. For example, the radiation therapy system may determine principal component weights that generate a deformation vector field that, when used to deform the primary reference image, are consistent with the treatment imaging data, wherein the principal component weights are assigned as the at least one parameter. For example, in the case where 2D slice imaging data is used as treatment imaging data, an optimization algorithm may be used to iteratively find the PCA weights that will generate a 3D image that, when sliced through the imaging plane to generate a 2D slice, agree as closely as possible with the imaging data. The same principle can be used when projection x-ray images are used, replacing slices with projections. Rather than needing to run an optimization for each acquired treatment image, another example is to first train a regression model between the treatment imaging data and the PCA weights, and then use this regression model to generate the PCA weights that would be expected to generate the measured imaging data.

In some examples in which the radiation therapy system generates the at least two reference images of the subject, the radiation therapy system may generate the at least two reference images from a 4D dataset, e.g., all of the 3D images in the 4D dataset, acquired with the subject set up for radiotherapy treatment, and prior to beam-on.

A tangible or non-tangible computer readable medium may be encoded with instructions that, when executed by a processor, cause the processor to perform the techniques described in this disclosure, including those described above with respect to FIG. 7. In addition, a radiotherapy system, such as shown in FIG. 1, can perform the computer-implemented method described above with respect to FIG. 7.

Figure 8:
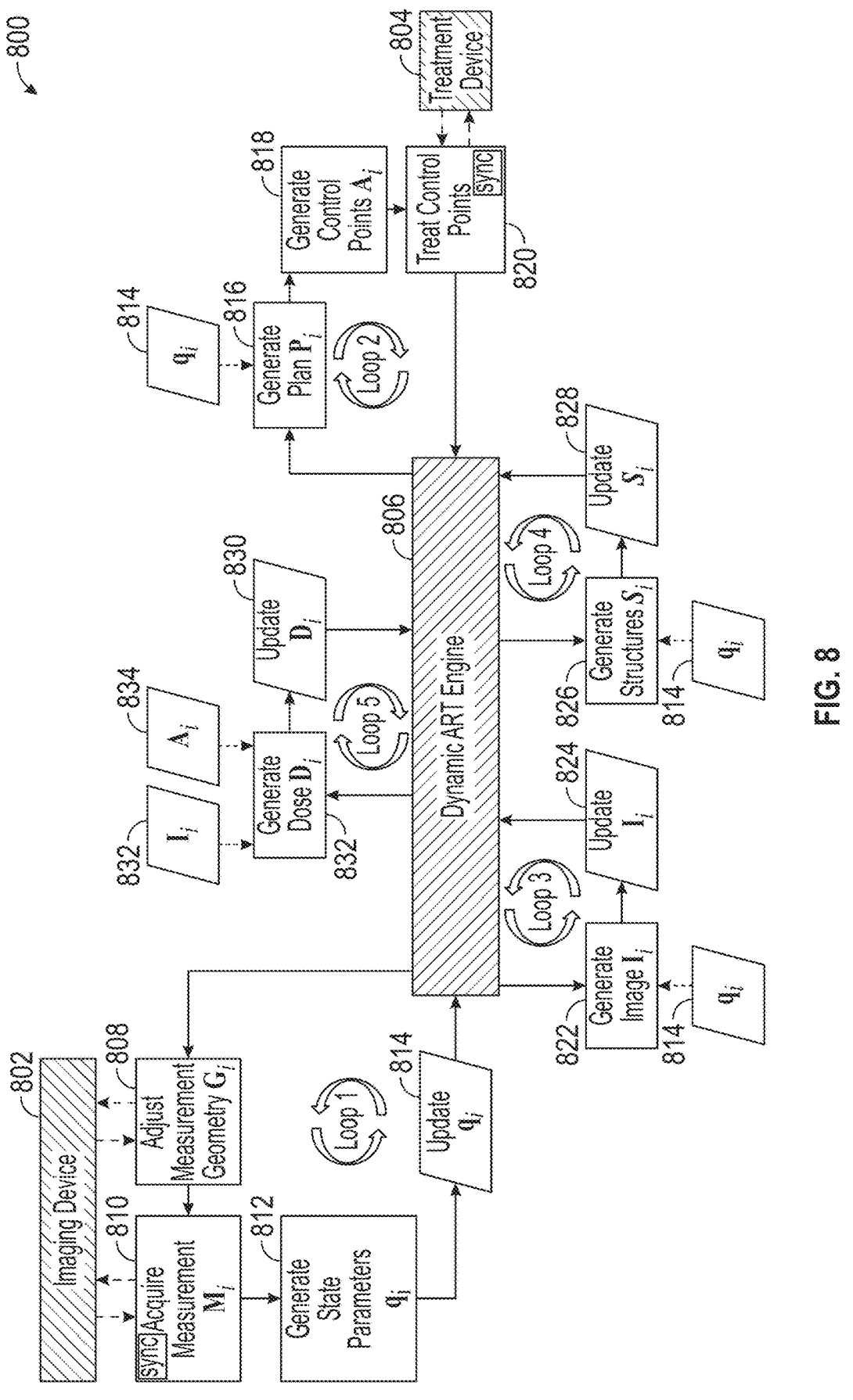
FIG. 8 is an example of a system that may execute a method for adaptation of a reference radiotherapy treatment plan having a plurality of control points, performed on a patient in a radiotherapy treatment session, according to some embodiments of the present disclosure.

FIG. 8 is an example of a system that may execute a method for adaptation of a reference radiotherapy treatment plan having a plurality of control points, performed on a patient in a radiotherapy treatment session, according to some embodiments of the present disclosure. The system 800, such as the radiotherapy system 100 of FIG. 1, may include an imaging device 802, such as the image acquisition device 132 of FIG. 1, that is configured to obtain imaging data of the patient. The system 800 may include a treatment device 804, such as the radiation therapy device 130 of FIG. 1, that is configured to deliver a dose of radiation to an anatomical region of interest of a patient using a current radiotherapy treatment plan. FIG. 8 represents the "beam-on" operation and relies on the first model, which was described above.

Many of the aspects for adapting the reference radiotherapy treatment plan using the techniques of this disclosure may be performed by a Dynamic Adaptive Radiation Therapy (ART) Engine 806, which may coordinate information exchange and processing. The information flow is represented as various computational "Loops", which can be repeatedly performed by a processor, such as the processor 114 of FIG. 1. The system 800 depicts five computational loops, namely Loop 1-Loop 5, but may include fewer than five loops or more than five loops. In some examples, loops other than those depicted may be added, such as safety and/or verification loops. In addition, there may be one or more loops within a loop, e.g., a subloop or substructure.

A processor may perform the loops in FIG. 1 at different rates. For example, a processor can perform loop 1 at a different rate than loop 2. The rate at which the processor performs the computations of a particular loop, e.g., loop 1, need not be a fixed rate. The different blocks in a loop may take different amounts of time each time that they are executed by the processor and the loop executes the next block as soon as the previous block is finished.

Loop 1 may adjust the measurement geometry $G_i$ at 808 and acquire a measurement $M_i$ at that geometry at 810, both of which are coordinated with the imaging device 802. The measurements $M_i$ may be used to generate the parameters $q_i$ at 812 from the previously trained function T. Loop 1 uses the first model described above and built during a training phase, for example, to sequentially generate the parameters $q_i$ from the measurements M. A memory device 814, such as the memory device 116 of FIG. 1, may store and be updated by the processor with the sequentially generated parameters $q_i$ while the processor is repeatedly performing the first computational loop.

Loop 1 may continuously repeat at a rate that is independent of a rate of the other loops. For example, a processor may perform a first computational loop, e.g., loop 1, to generate at least one parameter $q_i$ using the acquired measurements, wherein the at least one parameter represents an anatomical state of the subject and the processor may perform, at a second rate that is independent of the first rate, a second computational loop, e.g., loop 2, to generate a current radiotherapy treatment plan based on the at least one parameter $q_i$, where $q_i$ may be a vector that contains at least one parameter, e.g., q1, q2, and q3 if there are 3 parameters. the current radiotherapy treatment plan includes a plurality of control points, e.g., dose per beam, a position of a leaf of a multi-leaf collimator, and/or information defining a point along an aperture.

Loop 1 may be further broken down, such as subdivided into multiple sub-loops. For example, the measurements $M_i$ may continue to be acquired in parallel with the calculation and storing of the parameters $q_i$. Loop 1 may be used to determine parameters that represent the full 3D deformation of the patient.

A second computational loop, Loop 2, may use the sequentially generated parameters $q_i$ stored in the memory device 814 to generate a new radiotherapy treatment plan $P_i$ at 816 using the previously trained function R. Loop 2 uses the second model, e.g., a trained model, described above and built during a training phase, for example, to generate a new plan $P_i$ from the most recent value of parameters $q_i$. The control points at 818 may be generated from plan $P_i$ (e.g., the control points corresponding to those in the reference treatment plan that were currently intended to be delivered at the current time) and communicated to the treatment device for treatment. In other words, a processor can perform, at a second rate that is independent of the first rate, a second computational loop, e.g., loop 2, to generate a current radiotherapy treatment plan based on the at least one parameter $q_i$, where the current radiotherapy treatment plan includes a plurality of control points.

Now that the system 800 has the parameters $q_i$, the system 800 may use those parameters $q_i$ to modify the reference treatment plan for the radiotherapy treatment session during the radiotherapy treatment session by updating a control point of the reference radiotherapy treatment plan with the control point of the current radiotherapy treatment plan, such as by changing the control points as they are being delivered. That is, by using the techniques of this disclosure, as soon as the system 800 is about to provide a control point, the system 800 determines how to change that control point to better conform to the patient positioning at that moment.

When the system 800 determines a treatment plan, e.g., a sequence of control points, it determines, among other things, what beams are going to be combined to deliver the desired radiation dose distribution, which the system 800 may turn into a set of machine instructions that are control points that are sent to the linac and which are delivered one after another in sequence.

Loop 3 generates an image $I_i$ at 822 from the most recently stored value of parameter $q_i$ at 814, using the previously trained function Q, and stores it in memory device at 824.

Loop 4 generates the structure set $S_i$ at 826 from the most recently stored value of parameter $q_i$ at 814, using the previously trained function V, and stores it in memory at 828.

Loop 5 updates the cumulative dose distribution $D_i$ at 830 by calculating the generated dose at 832 from the delivered apertures at 834 onto the patient images $I_i$ at 836. This may be used to verify that the initially intended dose distribution is actually being delivered.

Because one or more loops may operate at different rates, it may be desirable to provide synchronization to 'phase lock' the calculations. For example, as illustrated by the two 'sync' boxes, it may be desirable to synchronize at least one of the control points of the current radiotherapy treatment plan with the acquired measurements. This may be done, for example, using a prediction algorithm to compensate for known lags in the calculations.

For example, in some examples, it may be desirable to synchronize, as closely as possible, a time stamp indicative of when the measurement M is acquired at block 810. The acquire measurement block 810 requests the image from the imaging device 802, but there may be a lag for the imaging device 802 to acquire the imaging data. In some examples, the imaging device 802 may return a time stamp that can be a synchronization point. The system 800 can synchronize that synchronization point to a time when the control point at block 820 will be modified on the treatment device. The "treat control points" block 820 controls the treatment device 804 to actually make that change on the hardware.

An example of synchronization is described as follows. When the processor calculates and stores the parameters $q_i$ in the memory device 814, the memory device 814 can also store a timestamp that links the parameter to a time when the actual image was acquired from the imaging device 802. When the processor generates the radiotherapy treatment plan at 816, the processor may not necessarily use the most recent value of the parameter $q_i$, but instead may use the history of the parameters $q_i$ that were stored to predict what value the parameter $q_i$ may take by the time loop 2 actually starts to modify the control point at the treatment device, and uses that predicted parameter $q_i$ to generate the treatment plan. Examples of prediction algorithms include normalized least squares, recursive least squares, multi-step linear methods, wavelet-based multiscale autoregression, support vector machines, extended Kalman filtering, neural networks, and kernel density estimation.

There may also be synchronization points in the other loops, but these may not be as importation because these loops are for display only and are not used to modify the treatment device, which may need to be accurately timed.

Figure 9:
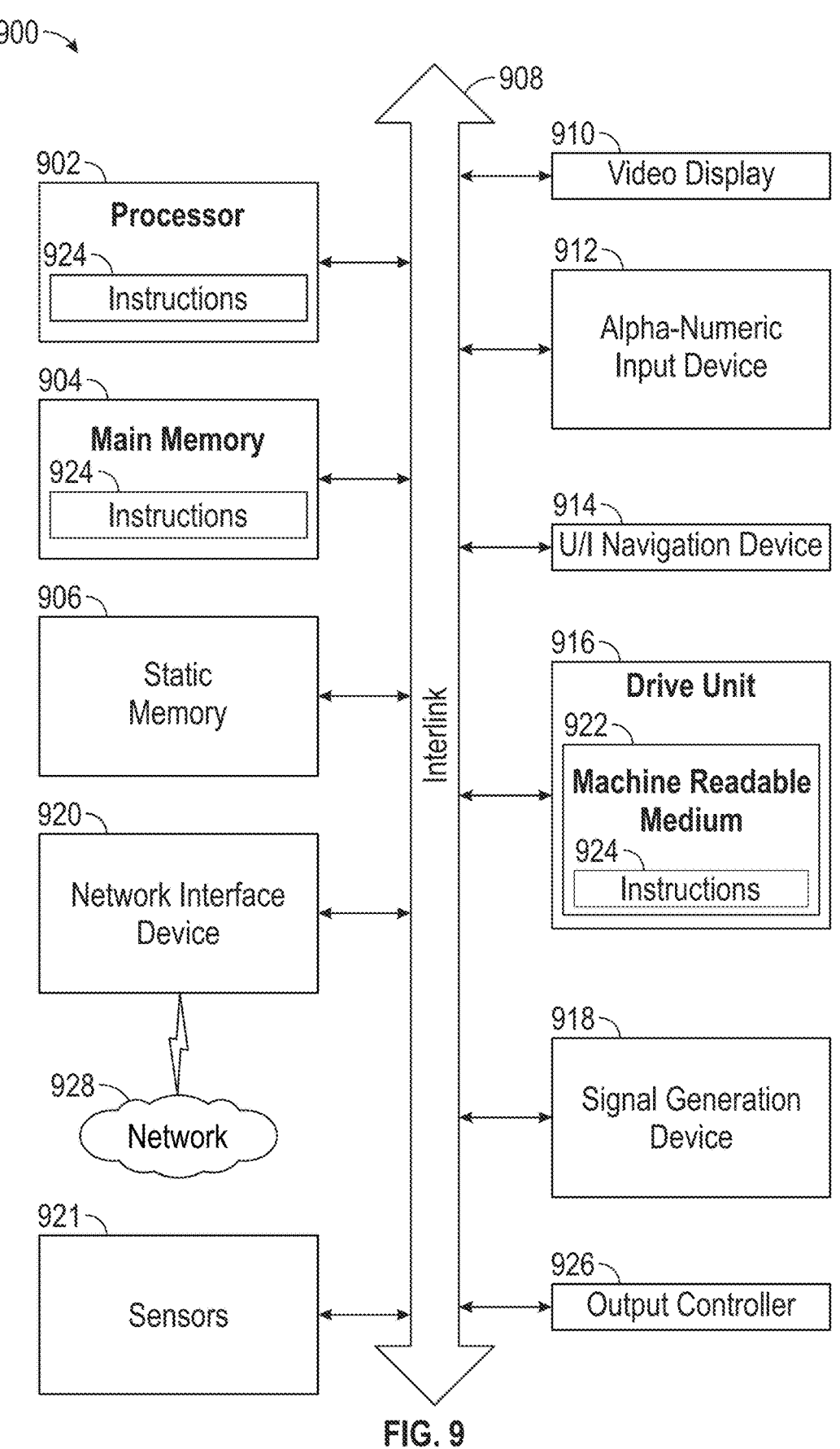
FIG. 9 illustrates an example of a block diagram of a machine on which one or more of the methods as discussed herein may be implemented.

FIG. 9 illustrates a block diagram of an embodiment of a machine 900 on which one or more of the methods as discussed herein may be implemented. In one or more embodiments, one or more items of the image processing device 112 may be implemented by the machine 900. In alternative embodiments, the machine 900 operates as a standalone device or may be connected (e.g., networked) to other machines. In one or more embodiments, the image processing device 112 may include one or more of the items of the machine 900. In a networked deployment, the machine 900 may operate in the capacity of a server or a client machine in server-client network environment, or as a peer machine in a peer-to-peer (or distributed) network environment. The machine 900 may be a personal computer (PC), a tablet PC, a set-top box (STB), a Personal Digital Assistant (PDA), a cellular telephone, a web appliance, a network router, switch or bridge, or any machine capable of executing instructions (sequential or otherwise) that specify actions to be taken by that machine. Further, while only a single machine 900 is illustrated, the term "machine" shall also be taken to include any collection of machines that individually or jointly execute a set (or multiple sets) of instructions to perform any one or more of the methodologies discussed herein.

The example machine 900 includes processing circuitry (e.g., the processor 902, a CPU, a GPU, an ASIC, circuitry, such as one or more transistors, resistors, capacitors, inductors, diodes, logic gates, multiplexers, buffers, modulators, demodulators, radios (e.g., transmit or receive radios or transceivers), sensors 921 (e.g., a transducer that converts one form of energy (e.g., light, heat, electrical, mechanical, or other energy) to another form of energy), or the like, or a combination thereof), a main memory 904 and a static memory 906, which communicate with each other via a bus 908. The machine 900 (e.g., computer system) may further include a video display unit 910 (e.g., a liquid crystal display (LCD) or a cathode ray tube (CRT)). The machine 900 also includes an alphanumeric input device 912 (e.g., a keyboard), a user interface (UI) navigation device 914 (e.g., a mouse), a disk drive or mass storage unit 916, a signal generation device 918 (e.g., a speaker), and a network interface device 920.

The disk drive or mass storage unit 916 includes a machine-readable medium 922 on which is stored one or more sets of data structures and instructions (e.g., software) 1124 embodying or utilized by any one or more of the methodologies or functions described herein. The instructions 924 may also reside, completely or at least partially, within the main memory 904 and/or within the processor 902 during execution thereof by the machine 900, the main memory 904 and the processor 902 also constituting machine-readable media.

The machine 900 as illustrated includes an output controller 926. The output controller 926 manages data flow to/from the machine 900. The output controller 926 is sometimes called a device controller, with software that directly interacts with the output controller 926 being called a device driver.

While the machine-readable medium 922 is shown in an embodiment to be a single medium, the term "machine-readable medium" may include a single medium or multiple media (e.g., a centralized or distributed database, and/or associated caches and servers) that store the one or more instructions 924 or data structures. The term "machine-readable medium" shall also be taken to include any tangible medium that is capable of storing, encoding, or carrying instructions for execution by the machine and that cause the machine to perform any one or more of the methodologies of the present disclosure, or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including by way of example semiconductor memory devices, e.g., Erasable Programmable Read-Only Memory (EPROM), EEPROM, and flash memory devices; magnetic disks such as internal hard disks and removable disks; magneto-optical disks; and CD-ROM and DVD-ROM disks.

The instructions 924 may further be transmitted or received over a communications network 928 using a transmission medium. The instructions 924 may be transmitted using the network interface device 920 and any one of a number of well-known transfer protocols (e.g., HTTP). Examples of communication networks include a LAN, a WAN, the Internet, mobile telephone networks, Plain Old Telephone (POTS) networks, and wireless data networks (e.g., WiFi and WiMax networks). The term "transmission medium" shall be taken to include any intangible medium that is capable of storing, encoding or carrying instructions for execution by the machine, and includes digital or analog communications signals or other intangible media to facilitate communication of such software.

As used herein, "communicatively coupled between" means that the entities on either of the coupling must communicate through an item therebetween and that those entities cannot communicate with each other without communicating through the item.

Additional Notes

The above detailed description includes references to the accompanying drawings, which form a part of the detailed description. The drawings show, by way of illustration but not by way of limitation, specific embodiments in which the disclosure may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a," "an," "the," and "said" are used when introducing elements of aspects of the disclosure or in the embodiments thereof, as is common in patent documents, to include one or more than one or more of the elements, independent of any other instances or usages of "at least one" or "one or more." In this document, the term "or" is used to refer to a nonexclusive or, such that "A or B" includes "A but not B," "B but not A," and "A and B," unless otherwise indicated.

In the appended claims, the terms "including" and "in which" are used as the plain-English equivalents of the respective terms "comprising" and "wherein." Also, in the following claims, the terms "comprising," "including," and "having" are intended to be open-ended to mean that there may be additional elements other than the listed elements, such that elements after such a term (e.g., comprising, including, having) in a claim are still deemed to fall within the scope of that claim. Moreover, in the following claims, the terms "first," "second," and "third," and so forth, are used merely as labels, and are not intended to impose numerical requirements on their objects.

Embodiments of the disclosure may be implemented with computer-executable instructions. The computer-executable instructions (e.g., software code) may be organized into one or more computer-executable components or modules. Aspects of the disclosure may be implemented with any number and organization of such components or modules. For example, aspects of the disclosure are not limited to the specific computer-executable instructions, or the specific components or modules illustrated in the figures and described herein. Other embodiments of the disclosure may include different computer-executable instructions or components having more or less functionality than illustrated and described herein.

Method examples (e.g., operations and functions) described herein may be machine or computer-implemented at least in part (e.g., implemented as software code or instructions). Some examples may include a computer-readable medium or machine-readable medium encoded with instructions operable to configure an electronic device to perform methods as described in the above examples. An implementation of such methods may include software code, such as microcode, assembly language code, a higher-level language code, or the like (e.g., "source code"). Such software code may include computer-readable instructions for performing various methods (e.g., "object" or "executable code"). The software code may form portions of computer program products. Software implementations of the embodiments described herein may be provided via an article of manufacture with the code or instructions stored thereon, or via a method of operating a communication interface to send data via a communication interface (e.g., wirelessly, over the internet, via satellite communications, and the like).

Further, the software code may be tangibly stored on one or more volatile or non-volatile computer-readable storage media during execution or at other times. These computer-readable storage media may include any mechanism that stores information in a form accessible by a machine (e.g., computing device, electronic system, and the like), such as, but are not limited to, floppy disks, hard disks, removable magnetic disks, any form of magnetic disk storage media, CD-ROMS, magnetic-optical disks, removable optical disks (e.g., compact disks and digital video disks), flash memory devices, magnetic cassettes, memory cards or sticks (e.g., secure digital cards), RAMs (e.g., CMOS RAM and the like), recordable/non-recordable media (e.g., ROMs), EPROMS, EEPROMS, or any type of media suitable for storing electronic instructions, and the like. Such computer-readable storage medium coupled to a computer system bus may be accessible by the processor and other parts of the OIS.

In an embodiment, the computer-readable storage medium may have encoded a data structure for a treatment planning, wherein the treatment plan may be adaptive. The data structure for the computer-readable storage medium may be at least one of a Digital Imaging and Communications in Medicine (DICOM) format, an extended DICOM format, an XML format, and the like. DICOM is an international communications standard that defines the format used to transfer medical image-related data between various types of medical equipment. DICOM RT refers to the communication standards that are specific to radiation therapy.

In various embodiments of the disclosure, the method of creating a component or module may be implemented in software, hardware, or a combination thereof. The methods provided by various embodiments of the present disclosure, for example, may be implemented in software by using standard programming languages such as, for example, Compute Unified Device Architecture (CUDA), C, C++, Java, Python, and the like; and using standard machine learning/deep learning library (or API), such as tensorflow, torch and the like; and combinations thereof. As used herein, the terms "software" and "firmware" are interchangeable, and include any computer program stored in memory for execution by a computer.

A communication interface includes any mechanism that interfaces to any of a hardwired, wireless, optical, and the like, medium to communicate to another device, such as a memory bus interface, a processor bus interface, an Internet connection, a disk controller, and the like. The communication interface may be configured by providing configuration parameters and/or sending signals to prepare the communication interface to provide a data signal describing the software content. The communication interface may be accessed via one or more commands or signals sent to the communication interface.

The present disclosure also relates to a system for performing the operations herein. This system may be specially constructed for the required purposes, or it may comprise a general-purpose computer selectively activated or reconfigured by a computer program stored in the computer. The order of execution or performance of the operations in embodiments of the disclosure illustrated and described herein is not essential, unless otherwise specified. That is, the operations may be performed in any order, unless otherwise specified, and embodiments of the disclosure may include additional or fewer operations than those disclosed herein. For example, it is contemplated that executing or performing a particular operation before, contemporaneously with, or after another operation is within the scope of aspects of the disclosure.

In view of the above, it will be seen that the several objects of the disclosure are achieved, and other beneficial results attained. Having described aspects of the disclosure in detail, it will be apparent that modifications and variations are possible without departing from the scope of aspects of the disclosure as defined in the appended claims. As various changes could be made in the above constructions, products, and methods without departing from the scope of aspects of the disclosure, it is intended that all matter contained in the above description and shown in the accompanying drawings shall be interpreted as illustrative and not in a limiting sense.

The above description is intended to be illustrative, and not restrictive. For example, the above-described examples (or one or more aspects thereof) may be used in combination with each other. In addition, many modifications may be made to adapt a particular situation or material to the teachings of the disclosure without departing from its scope. While the dimensions, types of materials and coatings described herein are intended to define the parameters of the disclosure, they are by no means limiting and are example embodiments. Many other embodiments will be apparent to those of skill in the art upon reviewing the above description. The scope of the disclosure should, therefore, be determined with reference to the appended claims, along with the full scope of equivalents to which such claims are entitled.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the disclosure should be determined with reference to the appended claims, along with the full scope of equivalents to which such claims are entitled. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

What is claimed is:

1. A computer-implemented method for adaptation of a reference radiotherapy treatment plan having a plurality of control points, performed on a subject in a radiotherapy treatment session, the computer-implemented method comprising:

obtaining treatment imaging data of the subject during the radiotherapy treatment session;

determining at least one parameter using the treatment imaging data;

generating a current radiotherapy treatment plan based on the at least one parameter;

modifying the reference radiotherapy treatment plan for the radiotherapy treatment session during the radiotherapy treatment session by updating one of the plurality of control points of the reference radiotherapy treatment plan with a control point of the current radiotherapy treatment plan; and using a trained model that includes:

generating at least two training images representing potential anatomical states of the subject, the at least two training images corresponding to at least two training parameters:

generating at least two training radiotherapy treatment plans corresponding to the at least two training images; and generating a training regression between the at least two training parameters and the at least two training radiotherapy treatment plans.

2. The computer-implemented method of claim 1, comprising:

generating a current image of the subject using the at least one parameter and a reference image.

3. The computer-implemented method of claim 2, comprising:

generating a current structure set of the subject using the at least one parameter and a reference structure set.

4. The computer-implemented method of claim 3, comprising:

generating a current dose distribution using the current radiotherapy treatment plan and the current image.

5. The computer-implemented method of claim 4, comprising:

generating a dose volume histogram using the current dose distribution and the current structure set.

6. The computer-implemented method of claim 1, wherein generating the current radiotherapy treatment plan based on at least one parameter includes:

generating, using the training regression, the current radiotherapy treatment plan from the at least one parameter.

7. The computer-implemented method of claim 1, wherein generating the at least two training radiotherapy treatment plans corresponding to the at least two training images includes:

modifying the reference radiotherapy treatment plan to the at least two training images using segment-aperture morphing.

8. The computer-implemented method of claim 1, comprising:

generating at least two reference images of the subject;

selecting one of the at least two reference images as a primary reference image;

generating a deformation vector field between the primary reference image and each of the other reference images; and determining at least one principal component of the deformation vector field.

9. The computer-implemented method of claim 8, wherein generating the at least two training images includes:

generating at least two deformation vector fields using the at least one principal component and at least two principal component weights; and generating the at least two training images by deforming the primary reference image using the at least two deformation vector fields.

10. The computer-implemented method of claim 8, wherein determining the at least one parameter includes:

determining principal component weights that generate a deformation vector field that, when used to deform the primary reference image, are consistent with the treatment imaging data, wherein the principal component weights are assigned as the at least one parameter.

11. The computer-implemented method of claim 8, wherein generating the at least two reference images of the subject includes:

generating the at least two reference images from a 4D dataset acquired with the subject set up for treatment, and prior to beam-on.

12. The computer-implemented method of claim 1, wherein an individual one of the control points includes aperture information.

13. The computer-implemented method of claim 1, wherein an individual one of the control points includes multi-leaf collimator leaf position information.

14. The computer-implemented method of claim 1, wherein an individual one of the control points includes dose rate information.

15. The computer-implemented method of claim 1, wherein obtaining the treatment imaging data of the subject during the radiotherapy treatment session includes:

obtaining the treatment imaging data of the subject during the radiotherapy treatment session using at least one of a kV imaging data, 2D MR slices, surface camera imaging data, cone-beam CT (CBCT) imaging data, or MV imaging data.

16. A radiotherapy system configured to perform the computer-implemented method of claim 1.

17. A tangible or non-tangible computer readable medium encoded with instructions that, when executed by a processor, cause the processor to perform the computer-implemented method of claim 1.

18. A radiotherapy system for adaptation of a reference radiotherapy treatment plan having a plurality of control points, performed on a subject in a radiotherapy treatment session, the radiotherapy system comprising:

an image acquisition device configured to acquire measurements of the subject during the radiotherapy treatment session;

a processor configured to:

perform, at a first rate, a first computational loop to generate at least one parameter using the acquired measurements, wherein the at least one parameter represents an anatomical state of the subject;

perform, at a second rate that is independent of the first rate, a second computational loop to generate a current radiotherapy treatment plan based on the at least one parameter, wherein the current radiotherapy treatment plan includes a plurality of control points; and modify a reference radiotherapy treatment plan for the radiotherapy treatment session during the radiotherapy treatment session by updating a control point of the reference radiotherapy treatment plan with the control point of the current radiotherapy treatment plan; and a radiotherapy device configured to deliver a dose of radiation to an anatomical region of interest using the current radiotherapy treatment plan.

19. The radiotherapy system of claim 18, wherein the processor is configured to:

repeatedly perform the first computational loop; and repeatedly perform the second computational loop.

20. The radiotherapy system of claim 19, comprising:

a memory storage device configured to store sequentially generated parameters while the processor is repeatedly performing the first computational loop, wherein the processor is configured to perform the second computational loop based on sequentially generated parameters.

21. The radiotherapy system of claim 20, wherein the processor is further configured to:

synchronize at least one of the control points of the current radiotherapy treatment plan with the acquired measurements.

22. The radiotherapy system of claim 18, wherein the processor is configured to:

perform, at a third rate that is independent of the first or second rates, a third computational loop to generate a current image of the subject using the most recent parameter.

23. The radiotherapy system of claim 18, wherein the processor is configured to:

perform, at a fourth rate that is independent of the first, second, or third rates, a fourth computational loop to generate a current dose distribution using the modified reference therapy plan with the updated control point and the current image.

24. The radiotherapy system of claim 18, wherein the processor is configured to:

perform, at a fifth rate that is independent of the first, second, third, or fourth rates, a fifth computational loop to generate a current structure set of the subject using the most recent parameter.

25. The radiotherapy system of claim 18, wherein the control point includes a dose per beam.

26. The radiotherapy system of claim 18, wherein the control point includes a position of a leaf of a multi-leaf collimator.

27. The radiotherapy system of claim 18, wherein the control point includes information defining a point along an aperture.

\* \* \* \* \*